(12) United States Patent
Suka et al.

(10) Patent No.: US 10,377,775 B2
(45) Date of Patent: Aug. 13, 2019

(54) METHOD FOR PRODUCING POLYALKYLENE GLYCOL DERIVATIVE HAVING AMINO GROUP AT END

(71) Applicant: Shin-Etsu Chemical Co., Ltd., Tokyo (JP)

(72) Inventors: Yuki Suka, Joetsu (JP); Yuji Harada, Joetsu (JP); Takeru Watanabe, Joetsu (JP); Shiori Nonaka, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 588 days.

(21) Appl. No.: 14/959,088

(22) Filed: Dec. 4, 2015

(65) Prior Publication Data

US 2016/0159831 A1  Jun. 9, 2016

(30) Foreign Application Priority Data

Dec. 4, 2014  (JP) .................................. 2014-246045
Jul. 30, 2015  (JP) .................................. 2015-151011

(51) Int. Cl.
| | |
|---|---|
| *C07F 7/10* | (2006.01) |
| *C07F 7/08* | (2006.01) |
| *C08G 65/12* | (2006.01) |
| *C08G 65/26* | (2006.01) |
| *C08G 65/333* | (2006.01) |

(52) U.S. Cl.
CPC .............. *C07F 7/0892* (2013.01); *C07F 7/10* (2013.01); *C08G 65/12* (2013.01); *C08G 65/2609* (2013.01); *C08G 65/33303* (2013.01); *C08G 65/33306* (2013.01); *Y02P 20/55* (2015.11)

(58) Field of Classification Search
CPC .......... C07F 7/0892; C07F 7/10; C08G 65/12; C08G 65/2609; C08G 65/33303; C08G 65/33306
USPC ....................................................... 556/423
See application file for complete search history.

(56) References Cited

U.S. PATENT DOCUMENTS

| | | |
|---|---|---|
| 4,504,622 A | 3/1985 | Schmitt |
| 5,021,585 A | 6/1991 | Dougherty et al. |
| 5,510,103 A | 4/1996 | Yokoyama et al. |
| 6,388,041 B1 | 5/2002 | Kataoka et al. |
| 6,455,639 B1 | 9/2002 | Yasukohchi et al. |
| 2001/0000510 A1 | 4/2001 | Sakurai et al. |
| 2006/0074200 A1 | 4/2006 | Daugs et al. |

(Continued)

FOREIGN PATENT DOCUMENTS

| | | |
|---|---|---|
| EP | 0555101 A2 | 8/1993 |
| EP | 1167418 A1 | 1/2002 |

(Continued)

OTHER PUBLICATIONS

Jia et al., Bioorganic & Medicinal Chemistry Letters 13 (2003) 2531-2534 (Year: 2003).*
Extended European Search Report corresponding to European Appilcation No. 15197846.7 dated Jul. 7, 2016.
Extended European Search Report corresponding to European Application No. 15197844.2 dated Aug. 9, 2016.
Yokoyama et al. "Synthesis of Poly(ethylene oxide) with Heterobifunctional Reactive Groups at Its Terminals by an Anionic Initiator", *Bioconjugate Chem.* 3:275-276 1992.
European Examination Report corresponding to European Application No. 15197846.7, dated Jul. 25, 2017. 7 pp.

(Continued)

*Primary Examiner* — Clinton A Brooks
*Assistant Examiner* — Kofi Adzamli
(74) *Attorney, Agent, or Firm* — Myers Bigel, P.A.

(57) ABSTRACT

A method simply produces a narrowly distributed and high-purity polyalkylene glycol derivative having an amino group at an end without using a heavy metal catalyst. A method for producing a polyalkylene glycol derivative having an amino group at the end by reacting a compound represented by the general formula (V) with an alkylene oxide, then reacting a reaction product with an electrophile represented by the general formula (I), and deprotecting the obtained product without using a heavy metal:

$$R_A^3O(R_A^4O)_{k-1}R_A^4O^-M^+ \qquad (V)$$

wherein $R_A^3$ represents a linear, branched, or cyclic hydrocarbon group having 1 to 20 carbon atoms; $R_A^4$ represents an alkylene group having 2 to 8 carbon atoms; k represents an integer of 2 to 5; and M represents an alkali metal;

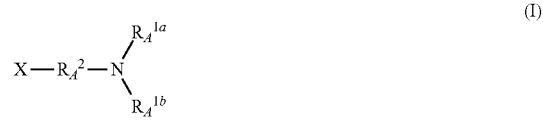

(I)

wherein $R_A^{1a}$ and $R_A^{1b}$ each independently represent a protective group of the amino group, or one of $R_A^{1a}$ and $R_A^{1b}$ represents H and the other represents a protective group of the amino group, or $R_A^{1a}$ and $R_A^{1b}$ bind to each other to form a cyclic protective group, and the protective group is deprotectable without using a heavy metal; $R_A^2$ represents a linear, branched, or cyclic hydrocarbon group having 1 to 6 carbon atoms; and X represents a leaving group.

16 Claims, No Drawings

(56) References Cited

U.S. PATENT DOCUMENTS

| | | | |
|---|---|---|---|
| 2007/0088081 A1 | 4/2007 | Phanstiel | |
| 2008/0188638 A1* | 8/2008 | Breitenkamp | C07D 273/01 528/393 |
| 2011/0136805 A1 | 6/2011 | Himmelsbach et al. | |
| 2011/0218322 A1 | 9/2011 | Nakamoto et al. | |
| 2013/0310555 A1 | 11/2013 | Chong | |
| 2016/0046762 A1 | 2/2016 | Yoshioka et al. | |

FOREIGN PATENT DOCUMENTS

| | | | | |
|---|---|---|---|---|
| EP | 2896643 A1 * | 7/2015 | | C08G 65/322 |
| JP | 04-182465 | 6/1992 | | |
| JP | 3507962 | 11/1994 | | |
| JP | 08-099979 | 4/1996 | | |
| JP | 08-134078 | 5/1996 | | |
| JP | 2690276 B2 | 12/1997 | | |
| JP | 2777530 B2 | 7/1998 | | |
| JP | 10-316690 | 12/1998 | | |
| JP | 11-335267 | 12/1999 | | |
| JP | 3050228 B2 | 6/2000 | | |
| JP | 3562000 | 6/2004 | | |
| JP | 2010-138388 | 6/2010 | | |
| JP | 4581248 B | 11/2010 | | |
| JP | 4987719 B2 | 7/2012 | | |
| JP | 2014-062050 | 4/2014 | | |
| JP | 2014-156400 | 8/2014 | | |
| WO | 96/22994 | 8/1996 | | |
| WO | 96/033162 | 10/1996 | | |
| WO | 98/043972 | 10/1998 | | |
| WO | 1999/057174 | 11/1999 | | |
| WO | 00/02877 | 1/2000 | | |
| WO | 2004/048316 | 6/2004 | | |
| WO | 2004/111094 | 12/2004 | | |
| WO | WO 2006/047419 A2 | 5/2006 | | |
| WO | WO-2006047419 A2 * | 5/2006 | | C07C 67/08 |
| WO | WO 2006047419 A2 * | 5/2006 | | C07C 67/08 |
| WO | WO 2007/127440 A2 | 11/2007 | | |
| WO | 2008/146172 | 12/2008 | | |
| WO | 2009/005671 | 1/2009 | | |
| WO | 2009/021965 | 2/2009 | | |
| WO | 2011/146336 | 11/2011 | | |
| WO | 2012/110986 | 8/2012 | | |
| WO | 2014/157117 | 10/2014 | | |

OTHER PUBLICATIONS

Japan Patent Office Action, JP 2015-151012, dated Apr. 27, 2018, 7 pages.

Japan Patent Office Action, JP 2015-151011, dated Apr. 24, 2018, 6 pages.

European Patent Office Examination Report, EP 15197846.7, dated May 8, 2018, 6 pages.

Takasu et al. "Chiral amine-silyl triflate complex mediated asymmetric intramolecular Michael-aldol reaction via a novel enanioselective enol silylation process" Chemical Communications (2000) No. 18, pp. 1739-1740.

Extended European Search Report corresponding to European Application No. 18185886.3, dated Aug. 29, 2018, 8 pages.

Extended European Search Report corresponding to European Application No. 18185868.9, dated Aug. 24, 2018, 6 pages.

Japan Patent Office Action, JP 2016-07737, dated Feb. 8, 2019, with English translation, 8 pages.

Corriu, Robert J. P. et al., Silyliron carbonyl complexes in organic synthesis: selective conversion of nitrils into N,N-bis (silyl) enamines, Organometallics, 1985, 4, 623-629.

Snider, Barry B. et al., Synthesis of a bicyclic model for the marine hepatotoxin cylindrospermospin, Tetrahedron Letters, 1995, Vo. 36 No. 26, 4587-4590.

Iwata, Masaaki et al., Design and synthesis of macromonocyclic polyamines composed of natural methylene arrays, Bulletin of the Chemical Society of Japan, 1989, vol. 62 No. 1, 198-210.

Miki, Yuya et al., Copper-catalyzed electrophilic amination of arylsilanes with hydroxylamines, Organic Letters, 2013, vol. 15 No. 1, 172-175.

* cited by examiner

METHOD FOR PRODUCING POLYALKYLENE GLYCOL DERIVATIVE HAVING AMINO GROUP AT END

RELATED APPLICATION

This application claims priority from Japanese Patent Application No. 2014-246045, filed Dec. 4, 2014 and Japanese Application No. 2015-151011, filed Jul. 30, 2015, the disclosures of which are incorporated by reference herein in their entirety.

FIELD AND BACKGROUND OF THE INVENTION

The present invention relates to a method for producing a polyalkylene glycol derivative having a terminal amino group.

Recently, in drug delivery systems, a method for encapsulating drugs in a polymer micelle using a block copolymer formed from a hydrophilic segment and a hydrophobic segment has been proposed (refer to, for example, Japanese Patent No. 2690276, Japanese Patent No. 2777530, and Japanese Patent Application Laid-Open No. 11-335267). By using the method, the polymer micelle functions as a carrier of drugs, producing various effects including sustained release of the drugs in vivo and concentrated dosage to an affected region.

As the hydrophilic segment, many examples with use of a polyalkylene glycol skeleton are proposed (refer to, for example, Japanese Patent No. 2690276, Japanese Patent No. 2777530, and Japanese Patent Application Laid-Open No. 11-335267). A compound having a polyalkylene glycol skeleton has low toxicity in vivo, and enables excretion by the kidney to be delayed. Consequently, in comparison with a compound having no polyalkylene glycol skeleton, the retention time in blood can be prolonged. As a result, with use of a drug micellized with a polyalkylene glycol derivative, the dosage amount or dosage frequency can be reduced.

Among polyalkylene glycol derivatives, a compound having an amino group at an end can lead to a block copolymer composed of a polyalkylene glycol skeleton and an amino acid skeleton through a ring-opening polymerization reaction with α-amino acid-N-carboxy anhydride. Many examples with use of the produced block copolymer for encapsulating drugs in a polymer micelle are proposed (refer to, for example, Japanese Patent No. 2690276, Japanese Patent No. 2777530, and Japanese Patent Application Laid-Open No. 11-335267).

Synthesis methods of such polyalkylene glycol derivatives having an amino group at an end are also known (refer to, for example, Japanese Patent No. 3050228 and Japanese Patent No. 3562000). In these methods, after polymerization of an alkylene oxide with use of a metal salt of monohydric alcohol as a polymerization initiator, a polymer end is converted to a hydroxyl group, and then to a 2-cyanoethoxy group, finally leading to an amino group-containing substituent group (3-amino-1-propoxy group) through hydrogen reduction of the cyano group.

A polymerization example of ethylene oxide in diglyme with use of a potassium salt of substituted diethylene glycol is known, and in this example, in order to dissolve the metal salt in a polymerization solvent, an excess amount of the alcohol that is an initiator raw material needs to remain during the synthesis of the metal salt. In addition, it is clearly disclosed that the necessary reaction temperature is 80 to 140° C. (see Japanese Patent No. 4987719).

SUMMARY OF THE INVENTION

It is difficult to completely dissolve the metal salts of monohydric alcohol used as a polymerization initiator in polymerization solvents (organic solvents such as, for example, tetrahydrofuran (abbreviated as "THF")) in many cases. In order to dissolve the metal salts in polymerization solvents, an excessive amount of alcohol that is a initiator raw material has to remain during synthesis of the metal salts (for example, in Japanese Patent No. 3050228, 13 mol of methanol to 2 mol of sodium methoxide that is a polymerization initiator, and in Japanese Patent No. 4987719, 0.209 mol of diethylene glycol monomethyl ether to 0.024 mol of a potassium salt of diethylene glycol monomethyl ether that is a polymerization initiator). Due to the presence of these alcohols in a reaction system, however, reduction in the polymerization rate is unavoidable. Consequently, crucial reaction conditions such as high temperature and high pressure are required for increasing the polymerization rate (refer to Japanese Patent No. 3050228 and Japanese Patent No. 4987719). Moreover, when the polymerization initiator does not dissolve in a polymerization solvent, the system does not become uniform, and therefore, there is a problem in that the dispersity of the obtained polyalkylene glycol derivative becomes broad because polymerization only progresses from the dissolved polymerization initiator.

Monohydric alcohols contain a trace amount of water in many cases. The polymerization of an alkylene oxide with a polymerization initiator prepared in a water-containing state produces a polymer compound having a hydroxyl group at both ends as by-product (hereinafter abbreviated as "diol polymer"). In the case of monohydric alcohols having a boiling point sufficiently higher than that of water, the water content can be reduced by dehydration under reduced pressure. Since methanol for use in the case in which an end is, for example, a methyl group, has a boiling point lower than that of water, the water content cannot be removed by dehydration under reduced pressure. The polymerization of an alkylene oxide with a metal salt prepared by using methanol, therefore, unavoidably produces a diol polymer. Since various physical properties of a diol polymer, such as structure and molecular weight, are similar to those of the target substance, it is extremely difficult to perform separation and purification. When the subsequent reactions proceed in the presence of a diol polymer as an impurity, a polymer including an amino group at both ends is produced unless proper reaction conditions are selected. The direct use of the polymer which includes such an impurity may make it possible that an intended performance cannot be achieved in designing a polymer micellizing agent. In the polymerization reaction, therefore, the water content is required to be reduced to be as low as possible.

Moreover, it is known that heavy metals have an adverse effect when excessively stored in vivo; however, in the synthesis methods described in Japanese Patent No. 3050228 and Japanese Patent No. 3562000, a cyano group is converted to an aminomethyl group through hydrogen reduction using Raney nickel catalyst, and therefore there is concern over the possibility that trace amounts of metals being mixed in the final product. Furthermore, the reaction is generally considered to require a high temperature, there have been problems yet to be solved that a target product cannot be obtained with a high yield rate because β-elimination of acrylonitrile progresses associated with reaction at a high temperature and that there is a risk that secondary and tertiary amines are produced due to addition reaction of an amine to an imine that is an intermediate in nitrile reduction.

It is an object of the present invention to provide a method for simply producing a narrowly distributed and high-purity polyalkylene glycol derivative having an amino group at an end under mild conditions without using a heavy metal catalyst by which method the problems of the conventional technologies are solved.

Through intensive research to achieve the object, the present inventors have found that, use of a compound, as a polymerization initiator, having a sufficient solubility in polymerization solvents accomplishes the polymerization of an alkylene oxide under mild conditions, and further that reaction of the obtained polymerization product with an electrophile the amino group which is protected can finally lead to a high-purity and narrowly distributed polyalkylene derivative having an amino group at an end through a simple process without using a heavy metal catalyst.

That is to say, the present invention relates to a method for producing a polyalkylene glycol derivative having an amino group at an end containing the following steps of (a) to (c).

(a) reacting a compound represented by the following general formula (V) with an alkylene oxide in a polymerization solvent:

$$R_A^3O(R_A^4O)_{k-1}R_A^4O^-M^+ \quad (V)$$

wherein $R_A^3$ represents a linear hydrocarbon group having 1 to 20 carbon atoms, or a branched or cyclic hydrocarbon group having 3 to 20 carbon atoms;

$R_A^4$ represents an alkylene group having 2 to 8 carbon atoms;

k represents an integer of 2 to 5; and

M represents an alkali metal;

(b) reacting a reaction product obtained in the step (a) with an electrophile represented by the following general formula (I):

wherein $R_A^{1a}$ and $R_A^{1b}$ each independently represent a protective group of the amino group, or one of $R_A^{1a}$ and $R_A^{1b}$ represents a hydrogen atom and the other represents a protective group of the amino group, or $R_A^{1a}$ and $R_A^{1b}$ bind to each other to represent a cyclic protective group forming a ring together with a nitrogen atom of the amino group, and the protective group represents a protective group deprotectable without using a heavy metal catalyst;

$R_A^2$ represents a linear divalent hydrocarbon group having 1 to 6 carbon atoms, or a branched or cyclic divalent hydrocarbon group having 3 to 6 carbon atoms; and X represents a leaving group; and (c) deprotecting a reaction product obtained in the step (b) without using a heavy metal catalyst.

The present invention, according to another embodiment, relates to a method for producing a polyalkylene glycol derivative having an amino group at an end containing the following [Step 1] to [Step 4]:

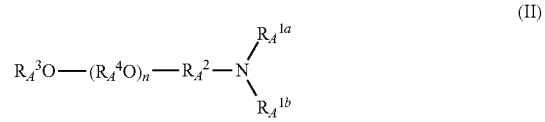

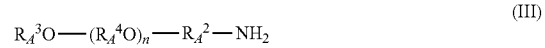

wherein $R_A^{1a}$ and $R_A^{1b}$ each independently represent a protective group of the amino group, or one of $R_A^{1a}$ and $R_A^{1b}$ represents a hydrogen atom and the other represents a protective group of the amino group, or $R_A^{1a}$ and $R_A^{1b}$ bind to each other to represent a cyclic protective group forming a ring together with a nitrogen atom of the amino group, and the protective group represents a protective group deprotectable without using a heavy metal catalyst;

$R_A^2$ represents a linear divalent hydrocarbon group having 1 to 6 carbon atoms, or a branched or cyclic divalent hydrocarbon group having 3 to 6 carbon atoms;

$R_A^3$ represents a linear hydrocarbon group having 1 to 20 carbon atoms, or a branched or cyclic hydrocarbon group having 3 to 20 carbon atoms;

$R_A^4$ represents an alkylene group having 2 to 8 carbon atoms;

X represents a leaving group; and n represents an integer of 3 to 450;

[Step 1]

a step of reacting a compound represented by the following general formula (IV) with an alkali metal or an alkali metal compound selected from M, $M^+H^-$, $R_X^-M^+$, $[R_Y]^{\bullet-}M^+$, and $R_ZO^-M^+$ (wherein M represents an alkali metal, $R_X$ represents an alkyl group having 1 to 20 carbon atoms or an arylalkyl group having 7 to 20 carbon atoms, $R_Y$ represents an aromatic compound that may have a substituent, and $R_Z$ represents an alkyl group having 1 to 6 carbon atoms) to obtain a compound represented by the following general formula (V):

$$R_A^3O(R_A^4O)_kH \quad (IV)$$

wherein $R_A^3$ and $R_A^4$ are the same as defined in the general formulas (II) and (III) as above;

k represents an integer of 2 to 5;

$$R_A^3O(R_A^4O)_{k-1}R_A^4O^-M^+ \quad (V)$$

wherein $R_A^3$, $R_A^4$, and k are the same as defined in the general formula (IV) as above; and M is the same as defined for the alkali metal or the alkali metal compound as above;

[Step 2]

a step of reacting the compound represented by the general formula (V) with an alkylene oxide in a polymerization solvent to obtain a compound represented by the following general formula (VI):

$$R_A^3O(R_A^4O)_{n-1}R_A^4O^-M^+ \quad (VI)$$

wherein $R_A^3$, $R_A^4$, and n are the same as defined in the general formulas (II) and (III) as above; and M is the same as defined for the alkali metal or the alkali metal compound as above;

[Step 3]

a step of reacting the compound represented by the general formula (VI) with the electrophile represented by the general formula (I) to obtain the compound represented by the general formula (II); and

[Step 4]

a step of deprotecting the compound represented by the general formula (II) without using a heavy metal catalyst to obtain the compound represented by the general formula (III).

The present invention provides a method for producing an amino group-containing polyethylene glycol derivative as a useful raw material for block copolymers for use in medical supplies and cosmetic products. By using the production method of the present invention, polymerization performed substantially in the absence of an alcohol, that is a polymerization initiator raw material and that is a cause of reduction in polymerization rate, becomes possible. Furthermore, the polymerization of an alkylene oxide can be performed under milder conditions than conventional conditions, and production of impurities such as a diol polymer attributable to a trace amount of water is suppressed to make it possible to produce a high-purity and narrowly distributed polyalkylene glycol derivative by a simple process. Moreover, in the case in which the method also includes a purification step, since freeze drying is not needed during the purification and extraction of the polyalkylene glycol derivative, the method is further advantageous in that the polyalkylene glycol derivative can be produced in an industrial scale and simplification of facilities and processes can be realized. Furthermore, by using the electrophile in which the amino group is protected, the reduction method using a heavy metal does not have to be used to prevent by-products being mixed, and therefore, it becomes possible to reduce a risk of mixing heavy metal impurities and by-products that should be avoided in medical supplies. Furthermore, since the polymerization initiator uniformly dissolves in the system during polymerization, the polyalkylene glycol derivative produced by the production method according to the present invention is narrowly distributed, capable of being extremely advantageously used in leading to a block copolymer formed from a hydrophilic segment and a hydrophobic segment, for use in a field of drug delivery system.

DETAILED DESCRIPTION OF PREFERRED EMBODIMENTS

The present invention now will be described more fully hereinafter in which embodiments of the invention are provided with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. Unless otherwise defined, all technical and scientific terms used herein have the same meaning as commonly understood by one of ordinary skill in the art to which this invention belongs. All references cited are incorporated herein by reference in their entirety.

The present invention is, according to an embodiment, a method for producing a polyalkylene glycol derivative having an amino group at an end represented by the following general formula (III), the method including the following [Step 2], [Step 3], and [Step 4]. Moreover, the present invention is, according to a preferable embodiment, a method for producing a polyalkylene glycol derivative having an amino group at an end represented by the following general formula (III), the method of sequentially performing the following [Step 1] to [Step 4]:

[Step 1]

A step of reacting a compound represented by the following general formula (IV) with an alkali metal or an alkali metal compound selected from M, $M^+H^-$, $R_X^-M^+$, $[R_Y]^{·-}M^+$, and $R_ZO^-M^+$ (wherein M represents an alkali metal, $R_X$ represents an alkyl group having 1 to 20 carbon atoms or an arylalkyl group having 7 to 20 carbon atoms, $R_Y$ represents an aromatic compound that may have a substituent, and $R_Z$ represents an alkyl group having 1 to 6 carbon atoms) to obtain a compound represented by the following general formula (V);

[Step 2]

a step of reacting the compound represented by the general formula (V) with an alkylene oxide in a polymerization solvent to obtain a compound represented by the following general formula (VI);

[Step 3]

a step of reacting the compound represented by the general formula (VI) with the electrophile represented by the general formula (I) to obtain the compound represented by the general formula (II); and

[Step 4]

a step of deprotecting the compound represented by the general formula (II) without using a heavy metal catalyst to obtain the compound represented by the general formula (III).

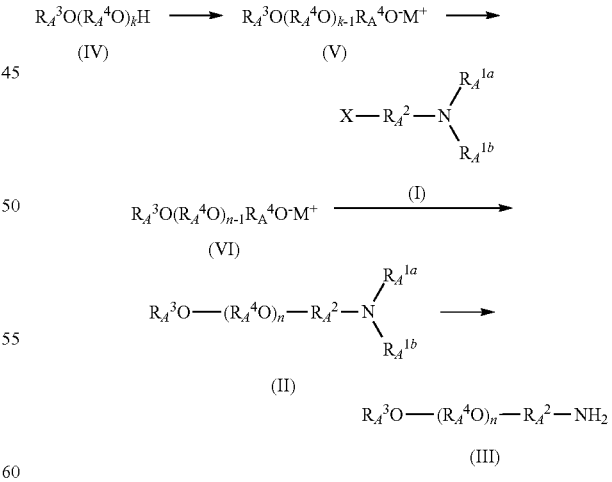

In the general formulas (I) and (II), $R_A^{1a}$ and $R_A^{1b}$ each independently represent a protective group of the amino group, or one of $R_A^{1a}$ and $R_A^{1b}$ represents a hydrogen atom and the other represents a protective group of the amino group, or $R_A^{1a}$ and $R_A^{1b}$ bind to each other to represent a cyclic protective group forming a ring together with a nitrogen atom of the amino group, and the protective group represents a protective group deprotectable without using a heavy metal catalyst. Specific examples of $R_A^{1a}$ and $R_A^{1b}$ are as described in the description of the [Step 3] below.

In the general formulas (I) to (III), $R_A^2$ represents a linear divalent hydrocarbon group having 1 to 6 carbon atoms, or a branched or cyclic divalent hydrocarbon group having 3 to 6 carbon atoms. Specific examples of $R_A^2$ include a group obtained by eliminating a hydrogen atom from each of a methyl group, an ethyl group, an n-propyl group, an isopropyl group, an n-butyl group, an isobutyl group, a tert-butyl group, an n-pentyl group, an n-hexyl group, a cyclopropyl group, a cyclobutyl group, a cyclopentyl group, and a cyclohexyl group, preferably a group obtained by eliminating a hydrogen atom from each of the ethyl group, and the n-propyl group.

In the general formulas (II) to (VI), $R_A^3$ represents a linear hydrocarbon group having 1 to 20 carbon atoms, or a branched or cyclic hydrocarbon group having 3 to 20 carbon atoms. Specific examples of $R_A^3$ include a methyl group, an ethyl group, an n-propyl group, an isopropyl group, an n-butyl group, an isobutyl group, a tert-butyl group, a pentyl group, a cyclopentyl group, a hexyl group, a cyclohexyl group, an octyl group, a decyl group, a dodecyl group, a phenyl group, an o-tolyl group, an m-tolyl group, ap-tolyl group, a 2,3-xylyl group, a 2,4-xylyl group, a 2,5-xylyl group, a 2,6-xylyl group, a 3,4-xylyl group, a 3,5-xylyl group, a mesityl group, a vinyl group, and an allyl group, preferably the methyl group and the ethyl group.

In the general formulas (II) to (VI), $R_A^4$ represents an alkylene group having 2 to 8 carbon atoms. Among others, alkylene groups having 2 to 3 carbon atoms are preferable. That is to say, an ethylene group or a propylene group is preferable. $(R_A^4O)_n$ may be composed of one kind of an oxyalkylene group, for example, only from an oxyethylene group or oxypropylene group, or may be two or more kinds of oxyalkylene groups mixed together. In the case in which two or more kinds of oxyalkylene groups are mixed together, $(R_A^4O)_n$ may be formed from two or more different kinds of oxyalkylene groups by random polymerization or block polymerization.

In the general formula (I), X represents a leaving group. Specific examples of X as the leaving group include Cl, Br, I, trifluoromethanesulfonate (hereinafter, written as "TfO"), p-toluenesulfonate (hereinafter, written as "TsO"), and methanesulfonate (hereinafter, written as "MsO"), although this is not limited thereto.

In the general formulas (II), (III), and (VI), n represents an integer of 3 to 450. Preferably n=10 to 400, more preferably n=20 to 350.

In the general formulas (IV) and (V), k=2 to 5. The repeating unit of $(R_A^4O)$ in the general formula (V) may have an effect of enhancing solubility to polymerization solvents, and k is preferably 2 or more from the viewpoint of the effect. Moreover, having k=2 to 4 is preferred considering that the compound represented by the general formula (IV) is made to be of high purity and to have a boiling point at which distillation is possible.

In the general formulas (V) and (VI), M represents an alkali metal. Specific examples of M as the alkali metal include lithium, sodium, potassium, cesium, and sodium-potassium alloy.

The embodiments will be described below in the order of [Step 1] to [Step 4] along time series.

In the [Step 1], the compound represented by the general formula (IV) is reacted with the alkali metal or the alkali metal compound to synthesize the compound represented by the following general formula (V).

$R_A^3O(R_A^4O)_kH$ (IV)

$R_A^3O(R_A^4O)_{k-1}R_A^4O^-M^+$ (V)

In the [Step 1], the alkali metal or the alkali metal compound to be reacted with the compound represented by the general formula (IV) means a substance selected from the group consisting of alkali metals represented by M, hydrides of alkali metals represented by $M^+H^-$, organic alkali metals represented by $R_X^-M^+$ or $[R_Y]^{·-}M^+$ ($R_X$ represents an alkyl group having 1 to 20 carbon atoms, or an arylalkyl group having 7 to 20 carbon atoms, and $R_Y$ represents an aromatic compound that may have a substituent), and alkali metal salts of monohydric alcohols represented by $R_Z O^-M^+$ ($R_Z$ represents an alkyl group having 1 to 6 carbon atoms).

Specific examples of M as the alkali metal include lithium, sodium, potassium, cesium, and sodium-potassium alloy. Specific examples of $M^+H^-$ include sodium hydride, and potassium hydride. Specific examples of $R_X^-M^+$ include ethyllithium, ethylsodium, n-butyllithium, sec-butyllithium, tert-butyllithium, 1,1-diphenylhexyllithium, 1,1-diphenyl-3-methylpentyllithium, 1,1-diphenylmethylpotassium, cumylsodium, cumylpotassium, and cumylcesium. Specific examples of $[R_Y]^{·-}M^+$ include lithium naphthalenide, sodium naphthalenide, potassium naphthalenide, anthracenelithium, anthracenesodium, anthracenepotassium, biphenylsodium, sodium 2-phenylnaphthalenide, phenanthrenesodium, sodium acenaphthylenide, sodium benzophenone ketyl, sodium 1-methoxynaphthalenide, potassium 1-methoxynaphthalenide, and potassium 1-methylnaphthalenide, and these compounds may be used singly or in combination of two or more. Specific examples of $R_Z$ in $R_Z O^-M^+$ include a methyl group, an ethyl group, an n-propyl group, an isopropyl group, an n-butyl group, a sec-butyl group, a tert-butyl group, an n-pentyl group, an isopentyl group, and an n-hexyl group, although this is not limited thereto. Among others, as alkali metal or the alkali metal compound, sodium, potassium, sodium hydride, and potassium hydride are preferred from the viewpoint that side reactions are suppressed, and moreover, sodium naphthalenide, potassium naphthalenide, anthracenesodium, anthracenepotassium, sodium methoxide, potassium methoxide, sodium ethoxide, and potassium ethoxide are preferred from the viewpoint of high reactivity.

The amount of the alkali metal, $M^+H^-$, $R_X^-M^+$ or $[R_Y]^{·-}M^+$ and/or $R_Z O^-M^+$ for use in the [Step 1] is, for example, 0.5 to 3.0 equivalents, more preferably 0.8 to 2.0 equivalents, more preferably 0.9 to 1.0 equivalents, relative to the number of moles of the compound represented by the general formula (IV). Particularly in the case in which the alkali metal compound used can also function as the polymerization initiator in the subsequent [Step 2], it is necessary to make the amount of the alkali metal compound used 1.0 equivalent or less. Moreover, in the case in which an alkali metal compound that produces an alcohol after reacting with an alcohol as an initiator raw material, such as, for example, potassium methoxide, it is also necessary to distill away methanol produced in the [Step 1] under reduced pressure after the synthesis of the compound represented by the general formula (V), and it is necessary that potassium methoxide produced through equilibrium reaction does not function as a polymerization initiator in the subsequent [Step 2].

In synthesizing the compound represented by the general formula (V) in the [Step 1], the reaction may be performed, for example, by adding the compound represented by the general formula (IV) and the alkali metal or the alkali metal compound to a proper solvent and mixing, or a mixture obtained by mixing the alkali metal or the alkali metal compound in a proper solvent may be dripped into the compound represented by the general formula (IV), or the compound represented by the general formula (IV) may be dripped into a mixture obtained by mixing the alkali metal or the alkali metal compound in a proper solvent. Specific examples of the solvent for use in the [Step 1] include ethers such as THF and 1,4-dioxane, and aromatic hydrocarbons such as benzene, toluene, and xylene. As the solvent, a solvent distilled with a dehydrating agent such as sodium metal may be used. The amount of the solvent used is, for example, 1 to 50 times, preferably 2 to 10 times, more preferably 2 to 5 times the mass of the compound represented by the general formula (IV), although this is not particularly limited thereto. The reaction in the [Step 1] is performed at a temperature of, for example, −78° C. to 150° C., preferably at a temperature of 0° C. to the reflux temperature of the solvent for use (for example, 0° C. to 66° C. as a reflux temperature of THF). The reaction system may be cooled or heated as needed.

Among others, as the solvent for use in the [Step 1], the same solvent as will be used as the polymerization solvent in the subsequent [Step 2] is preferably used. The reason is because whether the polymerization initiator synthesized in the [Step 1] dissolves or not in the polymerization solvent for use in the [Step 2] can be confirmed in advance during the synthesis of the polymerization initiator in the [Step 1]. Specifically, the solubility of the polymerization initiator in the polymerization solvent can be confirmed in a manner as described below in the case in which, for example, THF is used as the reaction solvent in the [Step 1], potassium hydride (for example, 1.0 equivalent or less of potassium hydride relative to the compound represented by the general formula (IV)) is used as the alkali metal compound, and THF is used as the polymerization solvent in the [Step 2]. As the reaction in the [Step 1] progresses, potassium hydride in a powder form decreases and hydrogen is produced. By confirming whether the precipitation of a salt and the cloudiness in the reaction solution are observed or not when all of the potassium hydride is finally reacted, without the precipitation of the polymerization initiator represented by the general formula (V) produced at that time in THF that is a reaction solvent in the [Step 1], the solubility of the polymerization initiator in the polymerization solvent in the subsequent [Step 2] can be confirmed in advance.

Moreover, as another method for confirming the solubility of the polymerization initiator represented by the general formula (V) in the polymerization solvent for use in the [Step 2], the method as described below can be given as an example, though not limited thereto. As described above, the compound represented by the general formula (IV) is reacted with the alkali metal or the alkali metal compound to synthesize the polymerization initiator represented by the general formula (V), and then the solvent and the reagents other than the polymerization initiator represented by the general formula (V) may be removed by a usual method to extract the polymerization initiator represented by the general formula (V). The obtained polymerization initiator represented by the general formula (V) may be dissolved in the polymerization solvent to be used in the subsequent [Step 2] at a concentration of, for example, 20 wt. %, and whether the precipitation of a salt and the cloudiness are observed or not can be confirmed by visual observation.

As described above, the polymerization of an alkylene oxide with a polymerization initiator prepared with a water-containing monohydric alcohol that is a polymerization initiator raw material produces a diol polymer as by-product. Separation of a diol polymer from the target substance is extremely difficult, and it is likely that the intended performance of a polymer micellizing agent is not achieved with the direct use of the polymer which contains a diol polymer or impurities derived therefrom. In the polymerization reaction in the subsequent [Step 2], therefore, the water content in the reaction system in which the compound (polymerization initiator) represented by the general formula (V) is dissolved is preferably reduced to be as low as possible. Regarding this, a compound represented by the general formula (IV) with, for example, $R_A{}^3$=$CH_3$, $R_A{}^4$=$CH_2CH_2$, k=2, and a high boiling point of 194° C., the compound being a precursor of the compound represented by the general formula (V), has a sufficient difference in boiling point from water, so that separation of water can be achieved by drying under reduced pressure. Therefore, it is preferred that, prior to the reaction of the compound represented by the general formula (IV) with the alkali metal or the alkali metal compound in the [Step 1], the compound represented by the general formula (IV) be sufficiently dried under reduced pressure and then distilled. In that case, the water content ratio of the compound represented by the general formula (IV) after distillation may be reduced, for example, to 50 ppm or less, preferably 10 ppm or less, more preferably 5 ppm or less. In this way, by reducing the water content of the compound represented by the general formula (IV) that is a raw material of the polymer initiator as low as possible, by-production of the diol polymer can more favorably be suppressed in performing polymerization using the obtained polymerization initiator.

In addition, the concentration of a substance (mmol/g) that can function as a polymerization initiator in a reaction solution (reaction solution after synthesis of the polymerization initiator) after completion of the [Step 1] can be determined from the amount of substance of the raw material alcohol for use in the [Step 1] and represented by the general formula (IV) and the total weight of the reaction solution after completion of the [Step 1]. That is to say, the concentration of the substance that can function as the polymerization initiator in the reaction solution after completion of the [Step 1] can be determined by "amount of substance of raw material alcohol (IV) used (mmol)/total weight of reaction solution (g) after completion of [Step 1]". The reason is because the raw material alcohol also functions as the polymerization initiator in the case in which the raw material alcohol represented by the general formula (IV) is left in the reaction solution after completion of the [Step 1]. (The reaction in the [Step 2] is equilibrium reaction, and therefore the compound represented the general formula (V) reacts as the polymerization initiator to produce a polymer, and an alkoxide at an end of the polymer eliminates a proton of the raw material alcohol (IV) to allow the raw material alcohol to function as an alkoxide (polymerization initiator).) However, as will be described later, the residual amount of the raw material alcohol in the reaction solution after completion of the [Step 1] is preferably as small as possible. The reaction solution after completion of the [Step 1] may be used as it is as a polymerization initiator solution in the subsequent [Step 2].

Conventionally, generally used polymerization initiators do not dissolve alone in polymerization solvents such as THF in many cases. For example, in the case in which polymerization of an alkylene oxide is performed in THF, $CH_3O^-M^+$ (M represents an alkali metal) that has conventionally been used when a methyl group is intended to be an end of polymerization does not singly dissolve in THF. Therefore, in the conventional method, in order to dissolve the polymerization initiator in the polymerization solvent to uniformly perform polymerization, it is necessary to use an excessive amount of methanol that is an alcohol as an initiator raw material. Due to the excessive presence of these alcohols in a reaction system, however, reduction in the polymerization rate is unavoidable. Consequently, crucial reaction conditions such as high temperature and high pressure are required for increasing the polymerization rate in the conventional method. In contrast, the compound represented by the general formula (V) for use as a polymerization initiator in the present invention is easily dissolved in the polymerization solvent such as THF without requiring an alcohol as an initiator raw material, enabling polymerization under mild conditions.

In this way, in order to obtain a sufficient polymerization rate under mild conditions in the subsequent [Step 2], a polymerization initiator having a small amount of a residual alcohol is preferably synthesized in the [Step 1]. Specifically, the ratio of the amounts of substances between the polymerization initiator represented by the general formula (V) and the alcohol that is an initiator raw material represented by the general formula (IV) is preferably 100:0 to 80:20 (mol %) after synthesis of the polymerization initiator represented by the general formula (V) from the alcohol as an initiator raw material represented by the general formula (IV), and more preferably reaction is performed so that the ratio is 100:0 to 90:10 (mol %). In order to achieve that, the [Step 1] is preferably performed under conditions so that the number of moles of the alkali metal or the alkali metal compound used is, for example, 0.8 to 1.5 times, preferably 0.9 to 1.0 times the number of moles of the compound used and represented by the general formula (IV). That is to say, a reaction product that has a small amount of residual alcohol as an initiator raw material is preferably obtained in the [Step 1].

Moreover, it is possible to distill away the alcohol represented by the general formula (IV) under reduced pressure after synthesis of the polymerization initiator represented by the general formula (V). In that case, the raw material alcohol is preferably removed until the ratio of the amounts of substances between the polymerization initiator represented by the general formula (V) and the alcohol represented by the general formula (IV) is 100:0 to 98:2 (mol %) after completion of the [Step 1], and more preferably the raw material alcohol is removed until the ratio is 100:0 to 99:1 (mol %). By reducing the amount of the residual raw material alcohol, it is possible to increase the polymerization rate in the subsequent [Step 2] more.

In the production method of the present invention, as described above, even when the alcohol compound, that is an initiator raw material and that is represented by the general formula (IV) and that is a factor of increasing the solubility of the polymerization initiator in polymerization solvents, and, on the other hand, also a factor of reducing the polymerization rate, is not left, it is possible to dissolve the compound represented by the general formula (V) as a polymerization initiator in polymerization solvents. A structure that plays the role is a repeating unit of $(RA_4O)$ in the general formula (V), and the compatibility between the polymerization initiator and the polymerization solvent is enhanced by the polymerization initiator having the structure, making it possible to dissolve the polymerization initiator in the polymerization solvent without a substantial presence of the alcohol. As a result thereof, polymerization in a uniform system becomes possible, and production of a narrowly distributed polyalkylene glycol derivative under mild conditions becomes possible.

In the [Step 2], the compound represented by the general formula (V) (polymerization initiator) is reacted with an alkylene oxide in the polymerization solvent to synthesize the compound represented by the following general formula (VI).

$$R_A^3O(R_A^4O)_{n-1}R_A^4O^-M^+ \quad\quad\quad (VI)$$

In the [Step 2], the compound represented by the general formula (V) may be reacted with an alkylene oxide after the compound represented by the general formula (V) is completely dissolved in the polymerization solvent. As described above, the compound represented by the general formula (V) can be easily soluble to the polymerization solvent even when the compound represented by the general formula (IV) that is the raw material alcohol is not substantially present. That the compound represented by the general formula (V) can completely be dissolved in the polymerization solvent can be confirmed by, for example, the fact that the precipitation of a salt or cloudiness is not observed in the polymerization solvent by visual observation. In this case, the precipitation of a salt and the cloudiness are not desirably observed in a state in which the mass of the polymerization solvent is equal to or less than 10 times (and equal to or more than 1 times) the mass of the compound represented by the general formula (V). That is to say, the precipitation of a salt and the cloudiness are not desirably observed in a state in which the concentration of the compound represented by the general formula (V) in the polymerization solvent solution is 9.1 wt. % or more (and 50 wt. % or less). After confirming that the compound represented by the general formula (V) completely dissolves in the polymerization solvent as described above, the polymerization solvent solution containing the compound represented by the general formula (V) may be used for polymerization reaction keeping the concentration as it is during the confirmation, or may be used for polymerization reaction in a diluted state by further adding the polymerization solvent. In addition, the amount of the polymerization solvent may be adjusted so as to be, for example, 1 to 50 times, preferably 2 to 25 times, the mass of the alkylene oxide used at the time of starting the polymerization reaction.

Furthermore, as described above, the presence of the raw material alcohol becomes the factor of reducing the polymerization rate, and therefore the polymerization initiator is preferably used in a state in which the amount of the raw material alcohol is small in the [Step 2]. For example, a reaction mixture containing the polymerization initiator represented by the general formula (V) obtained in the [Step 1] and the raw material alcohol represented by the general formula (IV) preferably in a ratio of the amounts of substances of 100:0 to 80:20 is preferably dissolved directly in the polymerization solvent to use.

As the polymerization solvent for use in the [Step 2], cyclic ether compounds having 4 to 10 carbon atoms or linear or branched ether compounds are preferably used from the viewpoint that the compatibility with the polymerization initiator is high. Specific examples of the cyclic ether compound includes furan, 2,3-dihydrofuran, 2,5-dihydrofuran, 2,3-dimethylfuran, 2,5-dimethylfuran, tetrahydrofuran (THF), 2-methyltetrahydrofuran, 3-methyltetrahydrofuran, 2,5-dimethyltetrahydrofuran, 1,2- methylenedioxybenzene, 1,3-dioxolane, 2-methyl-1,3-dioxolane, 4-methyl-1,3-dioxolane, 2,2-dimethyl-1,3-dioxolane, 3,4-dihydroxy-2H-pyran, tetrahydropyran, 1,3-dioxane, 1,4-dioxane, 2,4-dimethyl-1,3-dioxane, 1,4-benzodioxane, 1,3,5-trioxane, and oxepane, although this is not limited thereto. Specific examples of the linear or branched ether compound include monoethylene glycol dimethyl ether, diethylene glycol dimethyl ether, and triethylene glycol dimethyl ether, though not limited thereto. THF in particular is preferably used. Moreover, organic solvents other than the ether compounds may be used, and specific examples thereof include aromatic hydrocarbons such as benzene, toluene, and xylene, though not limited thereto. The organic solvent for use may be a single solvent, or may be used in combination of two or more. In the case in which the organic solvents are used in combination, the combination and the mixing ratio is not particularly limited.

The amount of the polymerization solvent used for polymerization reaction is, for example, 1 to 50 times, preferably 2 to 30 times, more preferably 3 to 20 times the mass of the alkylene oxide used, although this is not particularly limited. The polymerization solvent distilled with a dehydrating agent such as metal sodium is preferably used. The water content of the polymerization solvent is, for example, 50 ppm or less, preferably 10 ppm or less, more preferably 5 ppm or less.

Specific example of the alkylene oxide used includes ethylene oxide, propylene oxide, and butylene oxide. Among them, ethylene oxide and propylene oxide that are easily polymerized are preferred. The ratio of amounts of use between the compound represented by the general formula (V) and the alkylene oxide used for polymerization reaction is, for example, 1:1 to 1:448, preferably 1:10 to 1:400 as the ratio of the amounts of substances of the compound represented by the general formula (V): the alkylene oxide, although this is not particularly limited thereto.

In the [Step 2], the alkylene oxide may be added in one batch to a reaction system with the compound represented by the general formula (V) dissolved in the polymerization solvent, or a solution of the alkylene oxide dissolved in the polymerization solvent may be dripped into the reaction system. The polymerization reaction is performed at a temperature of, for example, 30° C. to 60° C., preferably 40° C. to 60° C., more preferably 45° C. to 60° C. The pressure during the polymerization reaction is, for example, 1.0 MPa or less, preferably 0.5 MPa or less. The degree of progress of polymerization reaction can be monitored with GPC, and when no change is observed in conversion ratio of the alkylene oxide, the completion can be assumed. The compound represented by the general formula (V) for use as a polymerization initiator in the present invention can be easily dissolved in the polymerization solvent as described above and requires no alcohol that is an initiator raw material, and thus does not require crucial reaction conditions such as high temperature and high pressure during the polymerization, enabling polymerization under mild conditions. As described above, use of the polymerization initiator represented by the general formula (V) makes it possible to obtain the polyalkylene glycol derivative represented by the general formula (VI) in the polymerization under mild conditions. Accordingly, the present invention also relates to a method for producing a polyalkylene glycol derivative represented by the general formula (VI) using a polymerization initiator represented by the general formula (V) (preferably including [Step 1] and [Step 2]).

In the [Step 3], the compound obtained in the preceding [Step 2] and represented by the general formula (VI) is reacted with the electrophile represented by the following formula (I) to synthesize the compound represented by the general formula (II).

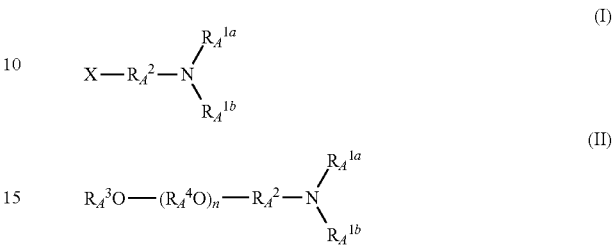

Preferably, in the [Step 3], an unpurified compound represented by the general formula (VI) obtained in the [Step 2] is directly used for the reaction with the electrophile represented by the general formula (I). This not only achieves cost reduction due to simplification of the separation purifying process, but also has an advantage of preventing reduction in yield rate due to purifying operation (polymer adhering to manufacturing equipment, dissolving in a poor solvent, and the like).

That is to say, in the [Step 3], the reaction liquid containing the compound represented by the general formula (VI) after completion of the [Step 2] may be directly used, or may be concentrated for use. In the case of concentration of the reaction liquid, the concentration of the compound represented by the general formula (VI) is concentrated to, for example, 10 to 50 mass %, preferably 15 to 45 mass %, more preferably 20 to 40 mass %. In the reaction in the [Step 3], the electrophile represented by the general formula (I) is added to the reaction liquid or concentrated liquid after completion of the [Step 2] to be reacted. As the addition method of the electrophile represented by the general formula (I) to a reaction system, the electrophile represented by the general formula (I) may be added in one batch to the reaction system, or a solution of the electrophile represented by the general formula (I) dissolved in an proper solvent may be dripped into the reaction system. Examples of the solvent used in this case include the same solvents as exemplified as the polymerization solvent in the [Step 2]. The amount of the electrophile represented by the general formula (I) used in this reaction is, for example, 1 to 20 equivalents, preferably 1 to 5 equivalents, more preferably 1 to 3 equivalents, relative to the number of moles of the compound represented by the general formula (VI).

Although the reaction in the [Step 3] proceeds without a catalyst, a basic compound may be added for further acceleration of the reaction. In that case, examples of the basic compound include potassium hydroxide, sodium hydroxide, and potassium tert-butoxide, though not limited thereto. The amount of the basic compound added is, for example, 1 to 10 equivalents, preferably 1 to 5 equivalents, more preferably 1 to 2 equivalents, relative to the number of moles of the compound represented by the general formula (VI).

In the [Step 3], the reaction is performed at a temperature of, for example, 30° C. to 60° C., preferably 30° C. to 50° C., more preferably 30° C. to 45° C. The reaction is monitored by NMR, and the completion can be assumed when no change is observed in conversion ratio.

In the [Step 3], the electrophile represented by the general formula (I) (sometimes referred to as "electrophile (I)" in the present Description) is used for the reaction with the compound represented by the general formula (VI) as described above. Since the compound represented by the general formula (I) is used as an electrophile in the [Step 3], there is an advantage that the nucleophilic reaction of the compound represented by the general formula (VI) may be completed only by using a relatively small amount of the electrophile. On the other hand, in the case in which acrylonitrile is used as an electrophile as in conventional technologies, a large excessive amount of the electrophile becomes necessary in some cases in order to allow the nucleophilic reaction of the compound represented by the general formula (VI) to progress up to 100%, and there is a possibility that polyacrylonitrile is by-produced. However such by-product is not produced in the present invention.

The electrophile (I) for use in the [Step 3] has an amino group protected by a protective group that may be deprotected without using a heavy metal catalyst as described above. Examples of the electrophile (I) may be given, for example, as classified into the following preferred electrophiles (I-I) to (I-IV) depending on the kind of the protective group represented by $R_A^{1a}$ and $R_A^{1b}$ in the general formula (I), though not limited thereto.

The electrophile (I-I) is an electrophile in the case in which $R_A^{1a}$ and $R_A^{1b}$ in the general formula (I) each independently represent a protective group of the amino group, or one of $R_A^{1a}$ and $R_A^{1b}$ is a hydrogen atom and the other is a protective group of the amino group, and is an electrophile in the case in which $R_A^{1a}$ and/or $R_A^{1b}$ are a protective group having a structure represented by $Si(R^1)_3$ (trialkylsilyl group).

In the structure represented by $Si(R^1)_3$, $R^1$ each independently represent a linear monovalent hydrocarbon group having 1 to 6 carbon atoms, or a branched or cyclic monovalent hydrocarbon group having 3 to 6 carbon atoms, or $R^1$ may bind to each other to form a 3 to 6 membered ring together with a silicon atom having bonds with $R^1$. Examples of $R^1$ include a methyl group, an ethyl group, an n-propyl group, an isopropyl group, an n-butyl group, an isobutyl group, a tert-butyl group, an n-pentyl group, an n-hexyl group, a cyclopropyl group, a cyclobutyl group, a cyclopentyl group, and a cyclohexyl group. Moreover, in the case in which $R^1$ bind to each other to form a ring together with a silicon atom, examples of $R^1$ include a group obtained by a hydrogen atom being eliminated from the above-listed groups.

Preferred specific examples of the protective group having a structure represented by $Si(R^1)_3$ include a trimethylsilyl group, a triethylsilyl group, and a tert-butyldimethylsilyl group, though not limited thereto.

The electrophile (I-II) is an electrophile in the cases in which $R_A^{1a}$ and $R_A^{1b}$ in the general formula (I) each independently represent a protective group of the amino group, or one of $R_A^{1a}$ and $R_A^{1b}$ is a hydrogen atom and the other is a protective group of the amino group, and is an electrophile in the case in which $R_A^{1a}$ and/or $R_A^{1b}$ are a protective group having a structure represented by $R_A^6 OCO$.

In the structure represented by $R_A^6 OCO$, $R_A^6$ represents a residue of a monovalent hydrocarbon having 1 to 20 carbon atoms, and the residue may contain a halogen atom, an oxygen atom, a nitrogen atom, a sulfur atom, a silicon atom, a phosphorus atom, or a boron atom.

Specific examples of the protective group having a structure represented by the formula $R_A^6 OCO$ include a methyloxycarbonyl group, an ethyloxycarbonyl group, an isobutyloxycarbonyl group, a tert-butyloxycarbonyl group, a tert-amyloxycarbonyl group, a 2,2,2-trichloroethyloxycarbonyl group, a 2-trimethylsilylethyloxycarboyl group, a phenylethyloxycarbonyl group, a 1-(1-adamantyl)-1-methylethyloxycarbonyl group, a 1,1-dimethyl-2-haloethyloxycarbonyl group, a 1,1-dimethyl-2,2-dibromoethyloxycarbonyl group, a 1,1-dimethyl-2,2,2-trichloroethyloxycarbonyl group, a 1-methyl-1-(4-biphenyl)ethyloxycarbonyl group, a 1-(3,5-di-t-butylphenyl)-1-methylethyloxycarbonyl group, a 2-(2'-pyridyl)ethyloxycarbonyl group, a 2-(4'-pyridyl)ethyloxycarbonyl group, a 2-(N,N-dicyclohexylcarboxyamide)ethyloxycarbonyl group, a 1-adamantyloxycarbonyl group, a vinyloxycarbonyl group, an allyloxycarbonyl group, a 1-isopropylallyloxycarbonyl group, a cinnamyloxycarbonyl group, a 4-nitrocinnamyloxycarbonyl group, a 8-quinolyloxycarbonyl group, a N-hydroxypiperidinyloxycarbonyl group, an alkyldithiocarbonyl group, a benzyloxycarbonyl group, a p-methoxybenzyloxycarbonyl group, a p-nitrobenzyloxycarbonyl group, a p-bromobenzyloxycarbonyl group, a p-chlorobenzyloxycarbonyl group, a 2,4-dichlorobenzyloxycarbonyl group, a 4-methylsulfinylbezyloxycarbonyl group, a 9-anthrylmethyloxycarbonyl group, a diphenylmethyloxycarbonyl group, a 9-fluorenylmethyloxycarbonyl group, a 9-(2,7-dibromo)fluorenylmethyloxycarbonyl group, a 2,7-di-t-butyl-[9-(10,10-dioxo-thioxanthenyl)]methyloxycarbonyl group, a 4-methoxyphenyloxycarbonyl group, a 2-methylthioethyloxycarbonyl group, a 2-methylsulfonylethyloxycarbonyl group, a 2-(p-toluenesulfonyl)ethyloxycarbonyl group, a [2-(1,3-dithianyl)]methyloxycarbonyl group, a 4-methylthiophenyloxycarbonyl group, a 2,4-dimethylthiophenyloxycarbonyl group, a 2-phosphonioethyloxycarbonyl group, a 2-triphenylphosphonioisopropyloxycarbonyl group, a 1,1-dimethyl-2-cyanoethyloxycarbonyl group, an m-chloro-p-acyloxybenzyloxycarbonyl group, a p-(dihydroxyboryl)benzyloxycarbonyl group, a 5-benzoisooxazolylmethyloxycarbonyl group, a 2-(trifluoromethyl)-6-chromonylmethyloxycarbonyl group, a phenyloxycarbonyl group, an m-nitrophenyloxycarbonyl group, a 3,5-dimethoxybenzyloxycarbonyl group, an o-nitrobenzyloxycarbonyl group, a 3,4-dimethoxy-6-nitrobenzyloxycarbonyl group, and a phenyl(o-nitrophenyl)methyloxycarbonyl group. Among them, the tert-butyloxycarbonyl group, the 2,2,2-trichloroethyloxycarbonyl group, the allyloxycarbonyl group, the benzyloxycarbonyl group, and the 9-flurorenylmethyloxycarbonyl group are preferred.

The electrophile (I-III) is an electrophile in the case in which $R_A^{1a}$ and $R_A^{1b}$ in the general formula (I) bind to each other to represent a cyclic protective group forming a ring together with a nitrogen atom of the amino group. Examples of the cyclic protective group in such an electrophile (I-III) include an N-phthaloyl group, an N-tetrachlorophthaloyl group, an N-4-nitrophthaloyl group, an N-dithiasucciloyl group, an N-2,3-diphenylmaleoyl group, an N-2,5-dimethylpyrrolyl group, an N-2,5-bis(triosopropyloxy)pyrrolyl group, an N-1,1,3,3-tetramethyl-1,3-disilaisoindolyl group, a 3,5-dinitro-4-pyridonyl group, a 1,3,5-dioxazinyl group, and a 2,2,5,5-tetramethyl-2,5-disila-1-azacyclopentane, although this is not limited thereto. Among them, the N-phthaloyl group is preferred.

The electrophile (I-IV) is an electrophile in the case other than: the case in which $R_A^{1a}$ and/or $R_A^{1b}$ represent the protective group of the electrophile (I-I) (protective group represented by $Si(R^1)_3$); the case in which $R_A^{1a}$ and/or $R_A^{1b}$ represent the protective group of the electrophile (I-II) (protective group having structure represented by $R_A^6 OCO$); and the case in which $R_A^{1a}$ and/or $R_A^{1b}$ represent the protective group of the electrophile (I-III) (a cyclic protective group in which $R_A^{1a}$ and $R_A^{1b}$ bind to each other and form a ring together with a nitrogen atom).

Examples of the protective group in such an electrophile (I-IV) include a benzyl group, a p-methoxybenzyl group, a p-toluenesulfonyl group, a 2-nitrobenzenesulfonyl group, a (2-trimethylsilyl)ethanesulfonyl group, an allyl group, a pivaloyl group, a methoxymethyl group, a di(4-methoxyphenyl)methyl group, a 5-benzosuberyl group, a trinylmethyl group, a (4-methoxyphenyl)diphenylmethyl group, a 9-phenylfluorenyl group, a [2-(trimethylsilyl)ethoxy]methyl group, and an N-3-acetoxypropyl group, although this is not limited to the protective groups. Among them, the benzyl group, the p-toluenesulfonyl group, 2-nitrobenzenesulfonyl group, and the allyl group are preferred.

The electrophile represented by the general formula (I) is preferably any one of the electrophiles (I-I) to (I-IV), and, among them, the electrophile represented by the general formula (I-I-I) is preferred. That is to say, the electrophile represented by the general formula (I) where $R_A^{1a}$ and $R_A^{1b}$ each independently represent a trialkylsilyl group is more preferred. Since both of the protective groups of the amino group are the trialkylsilyl groups, there is an advantage that deprotection in the subsequent [Step 4] is easy and the electrophile is stable in the basic reaction liquid in the [Step 3]. Moreover, there is also an advantage that the electrophile does not have a hydrogen atom as $R_A^{1a}$ or $R_A^{1b}$ and therefore unnecessary reaction is difficult to occur. Therefore, it becomes possible to more simply and stably produce a narrowly distributed and high-purity polyalkylene glycol derivative.

(I-I-I)

(in the general formula (I-I-I), $R^1$ is the same as $R^1$ in the electrophile (I-I), and $R_A^2$ and X are the same as $R_A^2$ and X in the general formula (I))

The electrophiles (I-I) to (I-IV) may be synthesized by various conventionally known methods. Examples of the method for synthesizing the electrophile (I-I) include protecting the amino group of an amine having a leaving group with a silylating agent. Specific examples of the amine having a leaving group include halogenated amines such as 3-bromopropylamine hydrobromate, and 3-chloropropylamine hydrochloric acid salt, although this is not limited thereto. Specific examples of the silylating agent include chlorotrimethylsilane, chlorotriethylsilane, trimethylsilyl trifluoromethanesulfonate, and triethylsilyl trifluoromethanesulfonate (hereinafter, written as "TESOTf"), though not limited thereto.

Examples of another method for synthesizing the electrophile (I-I) include a method in which an alcohol the amino group of which is silyl-protected is reacted with a sulfonic halide to convert a hydroxy group at an end to a leaving group. Specific examples of the alcohol the amino group of which is silyl-protected include 3-bis(trimethylsilyl)amino-1-propanol, and 3-bis(triethylsilyl)amino-1-propanol, though not limited thereto. Specific examples of the sulfonic halide include p-toluenesulfonyl chloride (hereinafter, written as "TsCl"), and methanesulfonyl chloride (hereinafter, written as "MsCl"), though not limited thereto.

Examples of the method for synthesizing the electrophile (I-II) include protecting the amino group of an amine having a leaving group with a carbamating agent, although this is not limited thereto. Specific examples of the amine having a leaving group include halogenated amines such as 3-bromopropylamine hydrobromate, and 3-chloropropylamine hydrochloric acid salt, though not limited thereto. Specific examples of the carbamating agent include di-tert-butyl dicarbonate, benzyl chloroformate, fluorenylmethyl chloroformate, 2,2,2-trichloroethyl chloroformate, and allyl chloroformate, though not limited thereto.

Examples of the method for synthesizing the electrophile (I-III) include a method in which an amino alcohol is reacted with a cyclic acid anhydride, and a cyclic imide alcohol produced is reacted with a sulfonic halide to convert a hydroxy group at an end to a leaving group, though not limited thereto. Specific examples of the cyclic acid anhydride include phthalic anhydride, specific examples of the amino alcohol include 3-amino-1-propanol, and specific examples of the cyclic imide alcohol include N-(3-hydroxypropyl)phthalimide, though not limited thereto. Specific examples of the sulfonic halide include TsCl, and MsCl, though not limited thereto.

Examples of the method for synthesizing the electrophile (I-IV) include a method in which an amino alcohol is reacted with corresponding protective groups each having a leaving group, and a protected amino alcohol produced is reacted with a sulfonic halide to convert a hydroxy group at an end to a leaving group, though not limited thereto. Specific examples of the protective group having a leaving group include benzyl bromide, TsCl, 2-nitrobenzene sulfonyl chloride, and allyl bromide, specific examples of the amino alcohol include 3-amino-1-propanol, and specific examples of the protected amino alcohol include 3-bisbenzylamino-1-propanol, 3-bis(p-toluenesulfonyl)amino-1-propanol, and 3-bis(nitrobenzenesulfonyl)amino-1-propanol, 3-bisallylamino-1-propanol, although this is not limited thereto.

The compound represented by the general formula (II) which is a reaction product of the [Step 3] may be extracted as a solid from the reaction liquid for use prior to the subsequent step. In that case, the reaction liquid after completion of the [Step 3] is, either directly or after concentration, dripped into a poor solvent to perform crystallization of the compound represented by the general formula (II). In the case of concentration, the concentration of the compound represented by the general formula (II) is adjusted to be, for example, 10 to 50 mass %, preferably 15 to 45 mass %, more preferably 20 to 40 mass %. Moreover, a salt produced through etherification reaction may be removed from the reaction liquid by filtration prior to crystallization to prevent impurities from mixing, so that a high-purity compound represented by the general formula (II) may be extracted.

The process of removing the salt produced through etherification reaction in the [Step 3] from the reaction liquid by filtration may directly be performed in the reaction solvent, or may be performed after solvent substitution with a good solvent. In that case, specific examples of the good solvent include ethers such as THF and 1,4-dioxane, aromatic hydrocarbons such as benzene, toluene, and xylene, esters such as ethyl acetate, n-butyl acetate, and γ-butyrolactone, ketones such as acetone, methyl ethyl ketone, and methyl isobutyl ketone, dimethyl sulfoxide (DMSO), N,N-dimethylformamide (DMF), and acetonitrile, though not limited thereto. Use of a solvent in which a salt is easy to precipitate may reduce salts that remain in a polymer, and therefore aromatic hydrocarbons such as benzene, toluene, and xylene are preferred. These solvents may be used singly or in combinations of two or more. In that case, the mixing ratio is not particularly limited.

The polymer produced in the [Step 3] contains a large amount of oxygen atoms in the structure, and therefore a salt produced in the etherification reaction is incorporated in the polymer in some cases. In that case, the salt may be removed using an adsorption material. As the adsorption material, an aluminum hydroxide (e.g. "KYOWADO 200" made by Kyowa Chemical Industry Co., Ltd.), a synthesized hydrotalcite (e.g. "KYOWADO 500" made by Kyowa Chemical Industry Co., Ltd.), a synthesized magnesium silicate (e.g. "KYOWADO 600" made by Kyowa Chemical Industry Co., Ltd.), a synthesized aluminum silicate (e.g. "KYOWADO 700" made by Kyowa Chemical Industry Co., Ltd.), and an aluminum oxide/magnesium oxide solid solution (e.g. "KW-2000" made by Kyowa Chemical Industry Co., Ltd. and "TOMITA AD 700NS" made by Tomita Pharmaceutical Co., Ltd.) are used, however the adsorption material is not limited thereto as long as the material has performance with which a salt can be removed. Among them, KW-2000 is preferred because of high ion trapping ability. The amount of the adsorption material used is, for example, 0.01 to 10 times, preferably 0.1 to 8 times, more preferably 0.3 to 6 times the mass of the compound represented by the general formula (II), although this is not particularly limited thereto. An adsorbent may be directly fed into the reaction liquid at the time of completion of the reaction of the compound represented by the general formula (IV) with the electrophile represented by the general formula (I), or may be fed into the reaction liquid after the reaction is completed and the produced alkali metal salt is filtered. The adsorbent may be removed by filtration after the reaction was performed for 0.5 to 6 hours after feeding the adsorbent, however the reaction time is not particularly limited. As a method of using the adsorption material, the adsorption material may be used as a batch system and added into the reaction solution to perform stirring, or the adsorption material may be used as a column system and the reaction solution may be allowed to pass through a column where the adsorption material is filled. Specific example of the solvent in the case of performing adsorption treatment include ethers such as THF and 1,4-dioxane, aromatic hydrocarbons such as benzene, toluene, and xylene, esters such as ethyl acetate, n-butyl acetate, and γ-butyrolactone, ketones such as acetone, methyl ethyl ketone, and methyl isobutyl ketone, dimethyl sulfoxide (DMSO), N,N-dimethylformamide (DMF), and acetonitrile, although this is not limited thereto. The aromatic, hydrocarbons such as benzene, toluene, and xylene are preferred for the purpose of enhancing the ability of adsorbing salts. These solvents may be used singly or in combinations of two or more. In that case, the mixing ratio is not particularly limited.

The unpurified compound represented by the general formula (IV) produced in the [Step 2] is preferably used directly for the reaction with the electrophile (I) in the [Step 3] as described above from the viewpoint of simplifying the processes ("embodiment not through purification"). That is to say, the electrophile (I) is preferably reacted in a state in which an anion is left after the [Step 2]. In this case, the compound represented by the general formula (II) is synthesized directly from the compound represented by the general formula (VI) as represented by (VI)→(II).

Alternatively, in the [Step 3], the reaction of the compound represented by the general formula (VI) produced in the [Step 2] is stopped with an acid compound or the like, the compound represented by the general formula (IX) obtained by the reaction is then purified, and is reacted with the electrophile (I), so that the compound represented by the general formula (II) may also be synthesized ("embodiment through purification"). That is to say, the electrophile (I) may be reacted after the reaction of the anion is once stopped with an acid or the like after the [Step 2]. Specifically, the reaction of the compound represented by the general formula (VI) is stopped by adding an acid compound or the like to the reaction liquid after completion of the [Step 2] to convert the compound represented by the general formula (VI) to the compound represented by the following general formula (IX). Subsequently, the produced compound represented by the following general formula (IX) is purified by, for example, crystallization performed by dripping into a poor solvent, and is extracted from the reaction system. Subsequently, the compound represented by the following general formula (IX) after purification thus extracted is reacted with the electrophile (I) under the presence of a basic compound, so that the compound represented by the general formula (II) may be produced. In this case, the compound represented by the following general formula (IX) is converted back again to the compound represented by the general formula (VI) through the reaction with the basic compound, and thereafter is reacted with the electrophile (I). That is to say, the compound represented by the general formula (II) is synthesized from the compound represented by the general formula (VI) via the compound represented by the general formula (IX) as represented by (VI)→(IX)→(VI)→(II).

(in the general formula (IX), $R_A^3$, $R_A^4$, and n are the same as $R_A^3$, $R_A^4$, and n in the general formulas (II) and (III))

In the embodiment through purification, whether the obtained compound represented by the general formula (IX) was able to be synthesized as a product as desired through the polymerization in the [Step 2] may be confirmed after stopping the reaction by, for example, performing analysis by 1H-NMR. Moreover, the reaction with the electrophile (I) is performed after a low molecular weight compound produced in the polymerization is removed from the reaction system by crystallization performed by dripping into a poor solvent, so that the conversion of the low molecular weight compound to a compound having an amino group through the reaction with the electrophile (I) can be prevented.

Specific examples of the acid compound for use in stopping of the reaction include carboxylic acids such as formic acid, acetic acid, propionic acid, succinic acid, citric acid, tartaric acid, fumaric acid, malic acid, and trifluoroacetic acid, inorganic acids such as hydrochloric acid, sulfuric acid, nitric acid, phosphoric acid, and perchloric acid, and sulfonic acids such as benzenesulfonic acid and p-toluenesulfonic acid, and solid acids such as AMBERLYST SERIES made by Organo Corporation, although this is not limited thereto. The amount of the acid compound used is, for example, 1 to 10 equivalents, preferably 1 to 5 equivalents, more preferably 1 to 2 equivalents, relative to the number of moles of a compound represented by the general formula (VI). These acid compounds may be used singly or in combinations of two or more. In that case, the mixing ratio is not particularly limited.

Alternatively, the reaction may be stopped by combinations of a protic compound such as an alcohol and water and a basic adsorption material. Specific examples of the protic compound include methanol, ethanol, n-propyl alcohol, isopropyl alcohol, n-butyl alcohol, sec-butyl alcohol, tert-butyl alcohol, and water, although this is not limited thereto. The amount of the protic compound used is, for example, 1 to 10 equivalents, preferably 1 to 5 equivalents, more preferably 1 to 2 equivalents, relative to the number of moles of the compound represented by the general formula (VI). These protic compounds may be used singly or in combinations of two or more. In that case, the mixing ratio is not particularly limited. Adsorption materials as described in the [Step 3] may be used, though not particularly limited thereto. The amount of the adsorbent used is, for example, 0.01 to 10 times, preferably 0.02 to 1 time, more preferably 0.03 to 0.5 times the mass of the compound represented by the general formula (VI), though not particularly limited.

Crystallization may be performed with a poor solvent directly after stopping the reaction, or crystallization may be performed after solvent substitution with a good solvent. In that case, specific examples of the good solvent include ethers such as THF and 1,4-dioxane, aromatic hydrocarbons such as benzene, toluene, and xylene, esters such as ethyl acetate, n-butyl acetate, and γ-butyrolactone, ketones such as acetone, methyl ethyl ketone, and methyl isobutyl ketone, dimethyl sulfoxide (DMSO), N,N-dimethylformamide (DMF), and acetonitrile, although this is not limited thereto. These solvents may be used singly or in combinations of two or more. In that case, the mixing ratio is not particularly limited. The concentration of the compound represented by the general formula (IX) after solvent substitution is, for example, 10 to 50 mass %, preferably 15 to 45 mass %, more preferably 20 to 40 mass %.

The poor solvent for use has a low solubility for the compound represented by the general formula (IX). Specific examples of the suitable poor solvent include hydrocarbon such as hexane, heptane, octane, nonane, decane, cyclopentane, cyclohexane, cycloheptane, and cyclooctane, and ethers such as diethyl ether, diisopropyl ether, and di-n-butyl ether. The amount of the poor solvent used is, for example, 5 to 100 times, preferably 5 to 50 times, more preferably 5 to 20 times the mass of a compound represented by the general formula (IX), although this is not particularly limited thereto. The poor solvents may be used singly or in combinations of two or more. Alternatively the poor solvent may be mixed with a different solvent for use. Examples of the different solvent for mixing include esters such as ethyl acetate, n-butyl acetate, and γ-butyrolactone, ketones such as acetone, methyl ethyl ketone, and methyl isobutyl ketone, hydrocarbons such as benzene, toluene, xylene, and cumene, ethers such as tetrahydrofuran, diethyl ether, and 1,4-dioxane, alcohols such as methanol, ethanol, isopropyl alcohol, and ethylene glycol monomethyl ether, dimethyl sulfoxide (DMSO), N,N-dimethylformamide (DMF), and acetonitrile, although this is not limited thereto. In the case of using a mixture of two or more solvents as a poor solvent, the mixing ratio is not particularly limited.

After precipitation of solid of the compound represented by the general formula (IX) by crystallization, the solid may be washed for purification as needed. The solvent for use in washing is desirably the same poor solvent as described above, although this is not particularly limited. The amount of the washing solvent used is also not particularly limited. The produced solid is dried under reduced pressure, so that a compound represented by the general formula (IX) can be extracted as solid. As described above, the reaction of the compound produced in the [Step 1] and [Step 2] are performed, and then the compound represented by the general formula (VI) produced in the [step 2] is stopped with an acid compound or a proton compound, so that the polyalkylene glycol derivative represented by the general formula (IX) can be obtained. That is to say, the present invention also relates to a method for producing a polyalkylene glycol derivative represented by the general formula (IX), the method containing the above-described steps.

Specific example of the basic compound for use in the subsequent reaction of the compound represented by the general formula (IX) with the electrophile (I) include potassium hydroxide, sodium hydroxide, and potassium tert-butoxide, although this is not limited thereto. The amount of the basic compound added is, for example, 1 to 10 equivalents, preferably 1 to 5 equivalents, more preferably 1 to 2 equivalents, relative to the number of moles of the compound represented by the general formula (IX).

Conditions during the reaction of the compound represented by the general formula (IX) with the electrophile (I), such as reaction temperature is the same as the conditions during the reaction of the compound represented by the general formula (VI) with the electrophile (I) in the embodiment not through purification, as described above. Moreover, in the case of the compound represented by the general formula (II) produced through the reaction of the compound represented by the general formula (IX) with the electrophile (I), the solid of the compound represented by the general formula (II) may be extracted for use prior to the subsequent step. However the extraction method is the same as the method for extracting the compound represented by the general formula (II) in the embodiment not through purification, as described above.

In the [Step 4], deprotection of the protective groups in the compound represented by the general formula (II) produced in the [Step 3] is performed. The deprotection is performed without using a heavy metal catalyst. The heavy metal catalyst here means a catalyst using a heavy metal such as, for example, Co, Ni, Pd, Pt, Rh, Ru, Cu, or Cr as a raw material.

In the [Step 4], the method for performing deprotection without using a heavy metal catalyst is not particularly limited, however, in the case in which $R_A^{1a}$ and/or $R_A^{1b}$ in the general formula (II) represent a silyl group (electrophile (I-I)), for example, water or an alcohol ($R^6OH$: in the formula, $R^6$ represents a hydrocarbon group having 1 to 5 carbon atoms) is reacted with the compound represented by the general formula (II) in the presence of an acid catalyst, so that the compound represented by the general formula (II) may be converted to the compound represented by the general formula (III). Specific examples of the acid catalyst for use include carboxylic acids such as formic acid, acetic acid, propionic acid, succinic acid, citric acid, tartaric acid, fumaric acid, malic acid, and trifluoroacetic acid, inorganic acids such as hydrochloric acid, sulfuric acid, nitric acid, phosphoric acid, and perchloric acid, and sulfonic acids such as benzenesulfonic acid and p-toluenesulfonic acid, and solid acids such as AMBERLYST SERIES made by Organo Corporation, although this is not limited thereto. The amount of the acid compound used is, for example, 0.01 to 1000 equivalents, preferably 0.1 to 100 equivalents, more preferably 1 to 10 equivalents, relative to the number of moles of the compound represented by the general formula (II). The acid compounds may be used singly or in combinations of two or more. In that case, the mixing ratio is not particularly limited.

In the case in which $R_A^{1a}$ and/or $R_A^{1b}$ represent a tert-butyloxycarbonyl group (electrophile (I-II)), for example, deprotection may be performed by allowing a strong acid such as trifluoroacetic acid and hydrochloric acid to act on the compound represented by the general formula (II). The amount of the strong acid used is, for example, 0.01 to 1000 equivalents, preferably 0.1 to 100 equivalents, more preferably 1 to 10 equivalents, relative to the number of moles of the compound represented by the general formula (II).

In the case in which $R_A^{1a}$ and $R_A^{1b}$ represent an N-phthaloyl group (electrophile (I-III)), for example, the phthaloyl group may be eliminated by reacting a hydrazine hydrate with the compound represented by the general formula (II) in an alcohol. Examples of the alcohol for use include methanol, ethanol, n-propyl alcohol, isopropyl alcohol, n-butyl alcohol, sec-butyl alcohol, and tert-butyl alcohol. The amount of the alcohol used is, for example, 1 to 100 times, preferably 3 to 50 times, more preferably 5 to 10 times the mass of the compound represented by the general formula (II). The amount of the hydrazine hydrate used is, for example, 1 to 50 equivalents, preferably 2 to 20 equivalents, more preferably 3 to 10 equivalents, relative to the number of moles of the compound represented by the general formula (II).

In the case in which $R_A^{1a}$ and/or $R_A^{1b}$ represent a benzyl group or an allyl group (electrophile (I-IV)), for example, deprotection of the compound represented by the general formula (II) may be performed under the condition of Birch reduction in which liquid ammonium and metal sodium are used. The amount of liquid ammonium used is, for example, 1 to 100 times, preferably 3 to 50 times, more preferably 5 to 10 times the mass of the compound represented by the general formula (II). The amount of metal sodium used is, for example, 2 to 50 equivalents, preferably 2 to 10 equivalents, more preferably 2 to 5 equivalents, relative to the number of moles of the compound represented by the general formula (II). As in the examples above, deprotection may be performed by appropriately selecting the condition where a heavy metal catalyst is not used, and the condition is not limited.

In the case in which deprotection is performed with an acid catalyst, a produced amine represented by the general formula (III) and an acid forms a salt, and the acid cannot be removed in some cases. In such cases, when a basic compound is added to the produced salt and is reacted with the acid, a salt of the added basic compound and the acid is formed, and therefore, the amine represented by the general formula (III) can be extracted. The produced salt can be removed by filtration. In the case in which the produced salt is incorporated into the polymer, the salt can be removed with an adsorption material. As the adsorption material, the adsorption materials as described in the above-mentioned [Step 3] may be used, though not particularly limited thereto. The amount of adsorbent used is, for example, 0.01 to 10 times, preferably 0.1 to 8 times, more preferably 0.3 to 6 times the mass of the compound represented by the general formula (III), though not particularly limited. Examples of the basic compound for use include potassium hydroxide, sodium hydroxide, potassium tert-butoxide, sodium methoxide, and potassium methoxide, though not limited thereto. The amount of the basic compound added is, for example, 1 to 10 equivalents, preferably 1 to 5 equivalents, more preferably 1 to 2 equivalents, relative to the number of moles of the acid catalyst for use in deprotection. As a solvent for use in filtration, the reaction solvent may directly be used, or filtration may be performed after solvent substitution with a solvent in which a salt is easy to precipitate. Specific examples of the solvent in which a salt is easy to precipitate include ethers such as THF and 1,4-dioxane, aromatic hydrocarbons such as benzene, toluene, and xylene, esters such as ethyl acetate, n-butyl acetate, and γ-butyrolactone, ketones such as acetone, methyl ethyl ketone, and methyl isobutyl ketone, dimethyl sulfoxide (DMSO), N,N-dimethylformamide (DMF), and acetonitrile, though not limited thereto. The aromatic hydrocarbons such as benzene, toluene, and xylene are preferred for the purpose of enhancing the filterability. These solvents may be used alone or in combination of two or more. In that case, the mixing ratio is not particularly limited.

In removing the acid catalyst, the adsorption material may directly be added to the reaction system without adding a basic compound, however, in that case, there is a possibility that the filterability is will decrease. Therefore, the adsorption material is preferably used after the above-mentioned addition of the basic compound.

Crystallization may be performed with a poor solvent directly after deprotection, or crystallization may also be performed after solvent substitution with a good solvent, or crystallization may also be performed after the above-mentioned reaction with the basic compound and the treatment with an adsorption material. Specific examples of the good solvent include ethers such as THF and 1,4-dioxane, aromatic hydrocarbons such as benzene, toluene, and xylene, esters such as ethyl acetate, n-butyl acetate, and γ-butyrolactone, ketones such as acetone, methyl ethyl ketone, and methyl isobutyl ketone, dimethyl sulfoxide (DMSO), N,N-dimethylformamide (DMF), and acetonitrile, though not limited thereto. These solvents may be used singly or in combinations of two or more. In that case, the mixing ratio is not particularly limited. The concentration of the compound after solvent substitution is, for example, 10 to 50 mass %, preferably 15 to 45 mass %, more preferably 20 to 40 mass %.

The poor solvent for use has a low solubility for the compound represented by the general formula (III). Specific examples of the suitable poor solvent for use include hydrocarbon such as hexane, heptane, octane, nonane, decane, cyclopentane, cyclohexane, cycloheptane, and cyclooctane, and ethers such as diethyl ether, diisopropyl ether, and di-n-butyl ether. The amount of the poor solvent used is, for example, 5 to 100 times, preferably 5 to 50 times, more preferably 5 to 20 times the mass of a compound represented by the general formula (III), although this is not particularly limited thereto. The poor solvents may be used singly or in combinations of two or more. Alternatively the poor solvent may be mixed with a different solvent for use. Examples of the different solvent for mixing include esters such as ethyl acetate, n-butyl acetate, and γ-butyrolactone, ketones such as acetone, methyl ethyl ketone, and methyl isobutyl ketone, hydrocarbons such as benzene, toluene, xylene, and cumene, ethers such as tetrahydrofuran, diethyl ether, and 1,4-dioxane, alcohols such as methanol, ethanol, isopropyl alcohol, and ethylene glycol monomethyl ether, dimethyl sulfoxide (DMSO), N,N-dimethylformamide (DMF), and acetonitrile, though not limited thereto. In the case of using a mixture of two or more solvents as a poor solvent, the mixing ratio is not particularly limited.

In the [Step 4], after precipitation of solid of the compound represented by the general formula (III) by crystallization, the solid may be washed for purification as needed. The solvent for use in washing is desirably the same poor solvent as described above, although this is not particularly limited. The amount of the washing solvent used is also not particularly limited. The produced solid is dried under reduced pressure, so that the compound represented by the general formula (III) can be extracted as solid.

In the present invention, the amino group is obtained by the deprotection as described above. Thus, by-products (compounds represented by the following (VII) to (IX)) that may be produced by, for example, a method described in Japanese Patent No. 3562000 are not substantially produced, and a narrowly distributed and high-purity polyalkylene glycol derivative having an amino group at an end, the polyalkylene glycol derivative represented by the general formula (III), may finally be synthesized. In contrast, in the case in which a cyanoethylated compound is subjected to hydrogen reduction to lead to a polyalkylene glycol derivative having an amino group by, for example, a method described in Japanese Patent No. 3562000, the hydrogen reduction is accompanied by β-elimination of acrylonitrile, and therefore, by-production of a PEG derivative represented by the following general formula (IX) and a polyacrylonitrile cannot be prevented. Moreover, there is a possibility that a secondary and tertiary amine compounds represented by the following general formula (VII) and (VIII) are produced in the hydrogen reduction process due to addition of an amine as a product to an imine as a reduction intermediate of nitrile in the conventional method. The side reactions may be suppressed by adding ammonia or acetic acid to the reaction system; however, it is difficult to completely control the side reactions by a conventional method.

(VII)

(VIII)

(IX)

(In the general formulas (VII) to (IX), $R_A^2$, $R_A^3$, $R_A^4$, and n are the same as $R_A^2$, $R_A^3$, $R_A^4$, and n in the general formulas (I) to (III))

The following [Step 5] to [Step 8] after the [Step 4] are optional purifying steps. In the case in which a protective group in the compound represented by the general formula (II) produced in the [Step 3] is a protective group that is deprotectable with an acid, deprotection may be performed in parallel by performing the [Step 5] to the [Step 8] after the [Step 3], so that the process can be further simplified. That is to say, in this case, the [Step 4] (the step of obtaining the compound represented by the general formula (III) by deprotecting the compound represented by the general formula (II)) may be performed specifically by the operation in the [Step 5] to the [Step 8]. Moreover, freeze drying is not necessary in the [Step 5] to [Step 8] as will be described below in purifying and extracting the compound represented by the general formula (III). Therefore, the method including the [Step 5] to [Step 8] has an advantage that simplification of facilities and processes can be realized in producing a polyalkylene glycol derivative on an industrial scale.

In the [Step 5], the reaction products produced in the [Step 3] or the [Step 4] are reacted with a strong acid cation exchange resin, and then the strong acid cation exchange resin is washed with water or monohydric alcohol having 1 to 5 carbon atoms for separation of substances other than the compound represented by the general formula (III).

Specific examples of the strong acid cation exchange resin for use in the [Step 5] include AMBERLITE series (IR120B, IR124B, 200CT, and 252) made by Organo Corporation, AMBERJET series (1020, 1024, 1060, and 1220) made by Organo Corporation, DIAION series (e.g. SK104, SK1B, SK110, SK112, PK208, PK212, PK216, PK218, PK220, PK228, UBK08, UBK10, UBK12, UBK510L, UBK530, and UBK550) made by Mitsubishi Chemical Corporation, DOWEX series (50 W×2 50-100, 50 W×2 100-200, 50 W×4 100-200, 50 W×8 50-100, 50 W×8 100-200, 50 W×8 200-400, HCR-S, and HCR-W2(H)) made by Dow Chemical Co., although this is not limited thereto. The amount of the strong acid cation exchange resin used is, for example, 1 to 50 times, preferably 1 to 30 times, more preferably 1 to 20 times the mass of the compound represented by the general formula (III).

In the case of using a strong acid cation exchange resin, the strong acid cation exchange resin may be treated with an acid compound prior to use. Since commercially available strong acid cation exchange resins are often in an alkali metal sulfonate salt state, the pretreatment with an acid compound regenerates sulfo groups, so that the reaction efficiency can be improved. In this case, examples of the acid compound for use include inorganic acids such as hydrochloric acid, sulfuric acid, nitric acid, phosphoric acid, and perchloric acid, although this is not limited thereto. The amount of the acid compound used is, for example, 1 to 15 times, preferably 1 to 10 times, more preferably 1 to 8 times the mass of the strong acid cation exchange resin. After treatment of the strong acid cation exchange resin with an acid compound, the acid compound is separated from the resin by water washing, and water is separated by a water-soluble organic solvent such as methanol and ethanol as needed.

Examples of the method for reacting the reaction products obtained in the [Step 3] or the [Step 4] with a strong acid cation exchange resin include: flowing the solution of the products in a column filled with the ion exchange resin to cause adsorption; and circulating the solution of crude products between a cartridge filled with the resin and the reaction tank for the [Step 3] or the [Step 4]; although this is not particularly limited. In the case in which the [Step 5] is performed after the [Step 3] directly, the compound represented by the general formula (II) is reacted with water or alcohol ($R^3OH$: in the formula, $R^3$ represents a hydrocarbon group having 1 to 5 carbon atoms) in the presence of a catalyst of the strong acid cation exchange resin, so that the compound represented by the general formula (III) may be adsorbed by the strong acid cation exchange resin after deprotection.

The strong acid cation exchange resin with the adsorbed compound represented by the general formula (III) is then washed with water or a monohydric alcohol having 1 to 5 carbon atoms, so that compounds other than the target substance can be separated. Examples of the monohydric alcohol having 1 to 5 carbon atoms include methanol, ethanol, n-propyl alcohol, isopropyl alcohol, n-butyl alcohol, sec-butyl alcohol, tert-butyl alcohol, n-pentyl alcohol, isopentyl alcohol, and neopentyl alcohol. In performing washing, water or a monohydric alcohol may be used singly, or a mixture of water and one or more alcohols or a mixture of two or more alcohols may be used. In that case, the mixing ratio is not particularly limited. The amount of water or a monohydric alcohol having 1 to 5 carbon atoms or a mixture thereof used is, for example, 1 to 30 times, preferably 1 to 20 times, more preferably 1 to 10 times the mass of the strong acid cation exchange resin for use, although this is not particularly limited.

In the [Step 6], the strong acid cation exchange resin with the adsorbed compound represented by the general formula (III) is reacted with a basic compound in water or a monohydric alcohol having 1 to 5 carbon atoms, so that a compound represented by the general formula (III) is extracted in water or the monohydric alcohol. In performing the reaction, water or the monohydric alcohol may be used singly, or a mixture of water and one or more alcohols or a mixture of two or more alcohols may be used. In that case, the mixing ratio is not particularly limited. Examples of the method for reacting a strong acid cation exchange resin and a basic compound include: flowing the solution of basic compound in a column filled with the ion exchange resin to cause reaction; and circulating the solution of the basic compound between a cartridge filled with the ion exchange resin and the reaction tank for the [Step 3], the [Step 4] and the [Step 5]; as described in the [Step 5], although this is not particularly limited.

Specific examples of the monohydric alcohol for use in the [Step 6] include methanol, ethanol, n-propyl alcohol, isopropyl alcohol, n-butyl alcohol, sec-butyl alcohol, tert-butyl alcohol, n-pentyl alcohol, isopentyl alcohol, and neopentyl alcohol. The amount of water or a monohydric alcohol used is, for example, 1 to 30 times, preferably 1 to 20 times, more preferably 1 to 10 times the mass of the strong acid cation exchange resin for use, although this is not particularly limited.

As the basic compound for use in the [Step 6], ammonia dissolved in water or an organic solvent (e.g. ammonia water and methanol solution of ammonia) may be suitably used, and primary, secondary and tertiary aliphatic amines, mixed amines, aromatic amines, and heterocyclic amines may be also used. Examples of the primary aliphatic amines include methylamine, ethylamine, n-propylamine, isopropylamine, n-butylamine, isobutylamine, sec-butylamine, tert-butylamine, and ethylene diamine; examples of the secondary aliphatic amines include dimethylamine, diethylamine, di-n-propylamine, diisopropylamine, di-n-butylamine, diisobutylamine, di-sec-butylamine; examples of the tertiary aliphatic amines include trimethylamine, triethylamine, tri-n-propylamine, triisopropylamine, tri-n-butylamine, triisobutylamine, and tri-sec-butylamine; examples of the mixed amines include dimethylethylamine, methylethylpropylamine, benzylamine, phenethylamine, benzyldimethylamine; specific examples of the aromatic amines and the heterocyclic amines include aniline derivatives (e.g. aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, and pyridine derivatives (e.g. pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 4-pyrrolidinopyridine, 2-(1-ethylpropyl)pyridine, aminopyridine, and dimethylaminopyridine), although this is not limited thereto. Alternatively an alkali aqueous solution such as potassium hydroxide and sodium hydroxide may be used as a basic compound. The amount of the basic compound used is, for example, 0.1 to 100 times, preferably 0.1 to 10 times, more preferably 0.1 to 5 times the mass of the strong acid cation exchange resin for use.

In the [Step 7], after concentration of the reaction liquid in the [Step 6], the solvent is substituted with a good solvent for a compound represented by the general formula (III) contained in the reaction liquid, such that the concentration of the compound represented by the general formula (III) is adjusted to be 10 to 50 mass %.

Examples of the good solvent for the compound represented by the general formula (III) for use in the [Step 7] include THF and the same good solvents as exemplified in the [Step 3], although this is not limited thereto. The good solvents may be used singly or in combinations of two or more. In that case, the mixing ratio is not particularly limited. After solvent substitution, the concentration of the compound is, for example, 10 to 50 mass %, preferably 15 to 45 mass %, more preferably 20 to 40 mass %.

In the [Step 8], the solution produced by concentration in the [Step 7] is dripped into a poor solvent for the compound represented by the general formula (III) to be precipitated. The compound represented by the general formula (III) is thereby produced.

The poor solvent for use in the [Step 8] has a low solubility for the compound represented by the general formula (III). Specific examples of the poor solvent include the same poor solvent as exemplified in the [Step 3] as described above, although this is not limited thereto. The amount of the poor solvent used is, for example, 5 to 100 times, preferably 5 to 50 times, more preferably 5 to 20 times the mass of the compound represented by the general formula (III), although this is not particularly limited. The poor solvent may be used singly, and alternatively the poor solvent may be mixed with a different solvent for use. Examples of the different solvent for mixing include the same different solvent as exemplified in the [Step 3] as described above, though not limited thereto. Moreover, in the case of mixing with a different solvent for use, the mixing ratio is not particularly limited.

In the [Step 8], after precipitation of solid by crystallization, the solid may be washed for purification as needed. Preferably the solvent for use in washing is the same poor solvent as described above, although this is not particularly limited. The amount of the washing solvent used is also not particularly limited. The produced solid is dried under reduced pressure, so that a compound represented by the general formula (III) can be extracted as solid.

In addition, in the case in which the compound represented by the general formula (III) is extracted as an aqueous solution in the operation after the [Step 6] (in the [Step 6] to [Step 8]), the compound represented by the general formula (III) may be extracted by freeze drying the aqueous solution. However, in this case, special facilities are required for freeze drying and a long time is required for complete removal of water, so that an industrial-scale production is difficult in some cases. In the present invention, however, the purification preferably using an organic solvent as described above allows for simplified facilities and processes.

Regarding the compound represented by the general formula (III) obtained after performing the [Step 1] to [Step 4] of the present invention, or obtained after performing the [Step 5] to [Step 8] subsequent to the [Step 1] to [Step 4] or the [Step 1] to [Step 3] of the present invention, a narrowly distributed polymer can be obtained because the initiation reaction is sufficiently faster than the propagation reaction during polymerization, the amount of water mixed as a factor of termination reaction is small, and further, the polymerization initiator is uniformly dissolved in the polymerization solvent.

That is to say, the compound represented by the general formula (III) produced by the production method of the present invention is narrowly distributed, and the dispersity (weight average molecular weight (Mw)/number average molecular weight (Mn)) is, for example, 1.0 to 1.20, preferably 1.0 to 1.10, more preferably 1.0 to 1.06. Moreover, the molecular weight of the compound represented by the general formula (III) produced by the production method of the present invention is preferably 5,000 to 25,000, more preferably 8,000 to 15,000 as the weight average molecular weight (Mw). The molecular weight and dispersity of a polymer in the present Description are defined as values obtained in the case in which measurement is performed with gel permeation chromatography (hereinafter, alleviated as "GPC").

The amount of by-products (VII) and (VIII) (compound represented by the general formula (VII) and compound represented by the general formula (VIII)) mixed in the product obtained after performing the [Step 1] to [Step 4], or in the product obtained after performing the [Step 5] to [Step 8] subsequent to the [Step 1] to [Step 4] or the [Step 1] to [Step 3] is preferably 3% or less, more preferably 1% or less expressed by an area content ratio (%) measured by GPC, relative to the total area of the compounds represented by the general formula (III), (VII), and (VIII). Most preferably, the obtained product does not contain any one of the compounds represented by the general formula (VII) and the compound represented by the general formula (VIII). According to the present embodiment, any one of the compounds represented by the general formula (VII) and the compounds represented by the general formula (VIII) are not actually produced.

The amount of by-product (IX) (compound represented by the general formula (IX)) mixed in the product obtained after performing the [Step 1] to [Step 4], or in the product obtained after performing the [Step 5] to [Step 8] subsequent to the [Step 1] to [Step 4] or the [Step 1] to [Step 3] is preferably 2 mol % or less, more preferably 1 mol % or less expressed by a content ratio in terms of composition ratio (mol %) measured by proton nuclear magnetic resonance (1H-NMR), relative to the total amount of substances of the compound represented by the general formula (III) and the compound represented by the general formula (IX). Most preferably, the obtained product does not contain a compound represented by the general formula (IX). According to the present embodiment, a compound represented by the general formula (IX) is not actually produced.

Moreover, the product obtained after performing the [Step 1] to [Step 4], or the product obtained after performing the [Step 5] to [Step 8] subsequent to the [Step 1] to [Step 4] or the [Step 1] to [Step 3] does not substantially contain such by-products (compounds represented by the general formulas (VII) to (IX) as described above. Preferably, $X_A/(X_A+X_B)$ is 0.95 or more, where $X_A$ represent the total amount of the main product (compound represented by the general formula (III)), $X_B$ represent the total amount of by-products, and both $X_A$ and $X_B$ are converted from the measurement results by GPC and 1H-NMR. Most preferably, the obtained product does not contain such by-products as described above.

The content of heavy metal impurities measured by a high frequency inductively coupled plasma mass spectrometer (ICP-MS) in the product obtained after performing the [Step 1] to [Step 4], or in the product obtained after performing the [Step 5] to [Step 8] subsequent to the [Step 1] to [Step 4] or the [Step 1] to [Step 3] is preferably 100 ppb or less, more preferably 10 ppb or less. The measurement of the amount of heavy metal impurities in a product is generally performed with the above-described ICP-MS, however the measurement method is not limited thereto. When analyzed with an ICP-MS, a polymer sample is diluted with a solvent for measurement. It is essential that a solvent used dissolve the polymer and not contain a metal. Ultrapure water and N-methyl-2-pyrrolidone for electronic industry are particularly preferred for the solvent; however, the solvent is not limited thereto. The dilution ratio is preferably 10 to 100,000 times, more preferably 50 to 1,000 times, though not limited thereto.

As described above, it is known that heavy metals, when accumulated in vivo, have adverse effects. In the conventional synthesis methods described in, for example, Japanese Patent No. 3050228 and Japanese Patent No. 3562000, a cyano group is converted to an aminomethyl group with a Raney nickel catalyst, there is concern that a heavy metal may be mixed in a product. According to "ICH Q3D: GUIDELINES FOR ELEMENTAL IMPURITIES Draft ICH consensus Guideline" reported in International Conference on Harmonization of Technical Requirements for Registration of Pharmaceuticals for Human Use, as elementary impurities that need risk assessment among elementary impurities, As, Pb, Cd, and Hg are listed in Class 1, V, Mo, Se, and Co are listed in Class 2A, Ag, Au, Tl, Pd, Pt, Ir, Os, Rh, and Ru are listed in Class 2B, and Sb, Ba, Li, Cr, Cu, Sn, and Ni are listed in Class 3. In the above conventional method, examples of the heavy metal for use in hydrogen reduction include Co, Ni, Pd, Pt, Rh, Ru, Cu, and Cr; however, these metals are listed as the metals that need risk assessment, and reducing the mixing amount thereof will be required more and more in the future.

In contrast, since the method of the present invention does not require the use of a heavy metal catalyst, there is no risk that a heavy metal will be mixed in a product. As a result thereof, the method of the present invention is a production method that is particularly suitable for obtaining a compound represented by the general formula (III) for use in medical supplies.

EXAMPLES

The present invention is specifically illustrated with reference to the following Examples and Comparative Examples, though the present invention is not limited to the following Examples. In the notation of molecular weight in Examples, the weight average molecular weight (Mw) and the number average molecular weight (Mn) are values in terms of polyethylene glycol measured by GPC. Measurement by GPC was performed under the following conditions:

Column: TSK gel Super AWM-H, Super AW-3000
Developing solvent: DMF (0.01 mol/L lithium bromide solution)
Column oven temperature: 60° C.
Sample concentration: 0.20 wt. %
Sample injection volume: 25 µl
Flow rate: 0.3 ml/min

[Synthesis Example 1] Synthesis of Polymerization Initiator (Va)

After placement of a stirring bar in a 500 mL two neck round-bottom flask, a rectification tube, a thermometer, a Liebig condenser, a fractionating column, two 50 mL round-bottom flasks, and one 300 mL two neck flask were connected, so that a distillation device was assembled. After the degree of vacuum in the device was held at 10 Pa or less, the internal part of the device was heated with an oil bath and a heat gun, so that the water content in the system was removed. Subsequently diethylene glycol monomethyl ether (made by Tokyo Chemical Industry Co., Ltd.) was injected into the 500 mL two neck round-bottom flask under nitrogen stream, and reduced-pressure distillation was performed. The measured water content ratio was 1 ppm or less after distillation (Measurement of the water content ratio was performed by a Karl Fisher moisture meter, and the same applies hereinafter).

After placement of a stirring bar in a 3 L two neck round-bottom flask, a rectification tube, a thermometer, a Dimroth condenser, a fractionating column, a 200 mL round-bottom flask, and a 2 L two neck flask were connected, so that a distillation device was assembled. After the degree of vacuum in the device was held at 10 Pa or less, the internal part of the device was heated with an oil bath and a heat gun, so that the water content in the system was removed. Subsequently dehydrated THF (made by Kanto Chemical Co., Ltd.), metal sodium pieces (made by Kanto Chemical Co., Ltd.), and benzophenone (made by Tokyo Chemical Industry Co., Ltd.) were injected into the 3 L two neck round-bottom flask under nitrogen stream, and refluxing was performed under normal pressure for 5 hours. After confirmation that the color in the 3 L two neck round-bottom flask changed into bluish purple, the distilled THF was extracted into the 2 L two neck flask. The measured water content ratio was 1 ppm or less after distillation.

In a glove box under nitrogen atmosphere, 15.98 g of potassium hydride (in a mineral oil form, made by Kanto Chemical Co., Ltd.) was weighed and fed into a 500 mL four neck flask connected to a thermometer, a dripping funnel, and a Dimroth condenser under nitrogen stream. After the mineral oil was washed with hexane to be separated, vacuum drying was performed for about two hours to obtain 6.193 g (154 mmol) of potassium hydride. Into the flask, 127.65 g of distilled THF was added with a syringe. Into the dripping funnel, 18.737 g (156 mmol) of distilled diethylene glycol monomethyl ether was injected to be dripped slowly. Maturation was performed for 2 hours, so that 148.62 g (1.05 mmol/g) of a THF solution of the polymerization initiator (Va) was produced. Precipitation of a salt and cloudiness were not observed at that time ((Va) mass/THF solution mass=16.6 wt. %). The ratio of the amounts of substances between the polymerization initiator (Va) synthesized by the above-described reaction and the alcohol that is an initiator raw material is 99:1 (mol %). A reaction scheme is shown in the following.

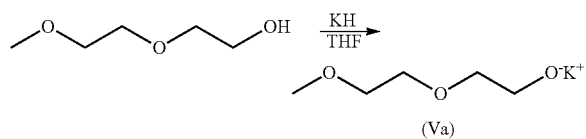

(Va)

[Synthesis Example 1-1] Synthesis of Polymerization Initiator (Va) by Another Method Distillation of diethylene glycol monomethyl ether and THF was performed in the same manner as in the [Synthesis Example 1]

In a glove box under nitrogen atmosphere, 1.28 g of naphthalene and 0.43 g of potassium were weighed and fed into a 100 mL three neck flask, and vacuum drying was performed for 1 hour. The flask was then brought back under a nitrogen atmosphere, and 13.58 g of distilled THF was added into the flask with a syringe. Stirring was performed for 1 hour to prepare a THF solution of potassium naphthalenide (0.65 mmol/g). On the other hand, 1.00 g of distilled diethylene glycol monomethyl ether was weighed with a syringe and fed into a 50 mL three neck flask under nitrogen atmosphere. 12.33 g of the THF solution of potassium naphthalenide prepared above was dripped thereto at normal temperature. Maturation was performed for 1 hour, so that 13.33 g (0.64 mmol/g) of a THF solution of the polymerization initiator (Va) was produced. Precipitation of a salt and cloudiness were not observed at that time ((Va) mass/THF solution mass=9.9 wt. %). The ratio of the amounts of substances between the polymerization initiator (Va) synthesized by the above-described reaction and the alcohol that is an initiator raw material is 96:4 (mol %). A reaction scheme is shown in the following.

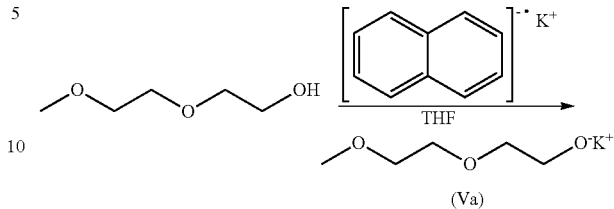

(Va)

[Synthesis Example 2] Synthesis of Electrophile (Ia)

(2-1) Synthesis of Silyl Protector (I-1)

In a 300 ml three neck flask, 6.0 g of 3-amino-1-propanol, 28.74 g of triethylamine, and 18.0 g of toluene were charged, and then 75.0 g of TESOTf was dripped therein under a nitrogen atmosphere. Stirring was then performed at 80° C. for 25 hours. The reaction liquid was transferred into a separatory funnel, the lower layer was separated, and the upper layer was distilled under reduced pressure, so that 31.47 g (yield rate 93.3%) of a silyl protector (I-1) was produced.

Silyl protector (I-1)
Colorless Liquid
Boiling point 133 to 138° C./10 Pa
$^1$H-NMR (500 MHz, CDCL3): δ=0.60 (18H, q), 0.94 (27H, t), 1.62 (2H, m), 2.83 (2H, m), and 3.54 (2H, t)

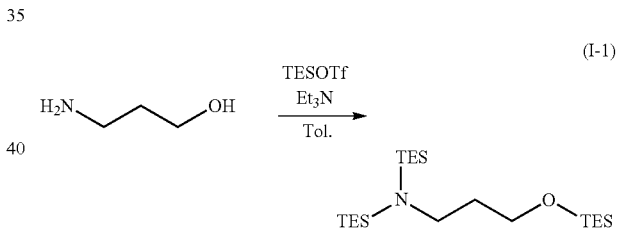

In the formula, TES means a triethylsilyl group.

(2-2) Synthesis of Alcohol Having Silyl-Protected Amino Group (I-2)

In a 200 ml one neck flask, 30.98 g of silyl protector (I-1), 30.98 g of methanol, and 0.2 g of sodium methoxide were charged, and stirring was performed at 60° C. for 18 hours. Triethylmethoxy silane was then distilled under reduced pressure, 30.98 g of methanol was again placed into the flask, and stirring was performed at 60° C. The same operation was repeated, then quenching was performed with sodium bicarbonate after completion of reaction, then solvent substitution with toluene was performed, and a salt was then removed by filtration. Toluene was then distilled away under reduced pressure, so that 22.66 g (crude yield rate 96.4%) of an alcohol having a silyl-protected amino group (I-2) was produced. The crude product had a sufficient purity as an intermediate, and was used directly for the subsequent step.

Alcohol having a silyl-protected amino group (I-2)
Colorless Liquid
$^1$H-NMR (500 MHz, CDCL3): δ=0.60 (12H, q), 0.93 (18H, t), 1.67 (2H, m), 2.85 (2H, m), and 3.59 (2H, m)

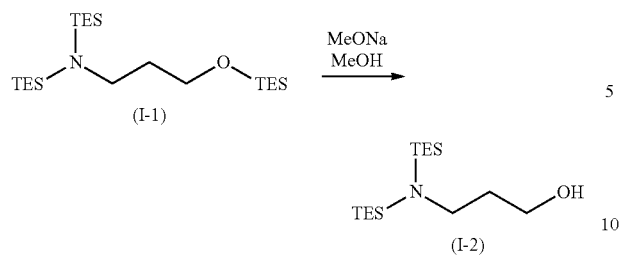

(2-3) Synthesis of Electrophile (Ia)

In a 50 ml three neck flask, 14.7 g of TsCl, 5 g of methylene chloride, and 5.0 g of triethylamine were charged, and a solution of 5.0 g of the alcohol having a silyl-protected amino group (I-2) dissolved in 10.0 g of methylene chloride was dripped therein while the flask was ice-cooled. The temperature was brought back to normal temperature, stirring was performed for 13 hours, then quenching was performed with water, and then extraction was performed with toluene. The toluene solution was then concentrated, so that 7.6 g (crude yield rate 100%) of an electrophile (Ia) was produced. The crude product had a sufficient purity as an intermediate, and was used directly for the subsequent step.

Electrophile (Ia)

Brown Liquid $^1$H-NMR (500 MHz, CDCL$_3$): δ=0.54 (12H, q), 0.89 (18H, t), 1.68 (2H, m), 2.45 (3H, s), 2.71 (2H, m), and 3.98 (2H, t)

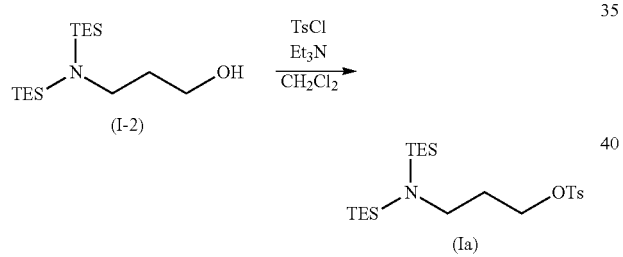

[Synthesis Example 3] Synthesis of Electrophile (Ib)

In a 200 ml three neck flask, 15.93 g of 3-bromopropylamine hydrobromate, 27.26 g of triethylamine, and 47.79 g of toluene were charged, and 50.00 g of TESOTf was then dripped therein under nitrogen atmosphere. Stirring was then performed at 80° C. for 63 hours. The reaction solution was transferred to a separatory flask, the lower layer was separated, and the upper layer was distilled under reduced pressure, so that 8.00 g (yield rate 30.0%) of an electrophile (Ib) was produced.

Electrophile (Ib)

Colorless Liquid

Boiling point 108° C./30 Pa $^1$H-NMR (500 MHz, CDCL$_3$): δ=0.61 (12H, q), 0.94 (18H, t), 1.92 (2H, m), 2.90 (2H, m), and 3.31 (2H, t)

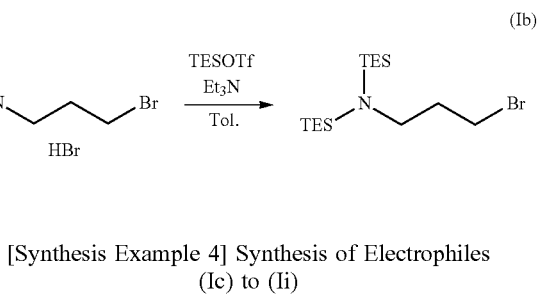

[Synthesis Example 4] Synthesis of Electrophiles (Ic) to (Ii)

The following electrophiles (Ic) to (Ii) were synthesized in the same manner as in, the [Synthesis Example 3], except that TESOTf was changed to corresponding protecting agents.

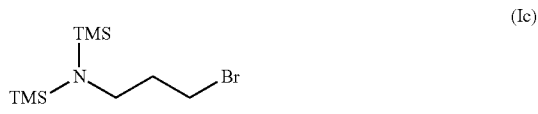

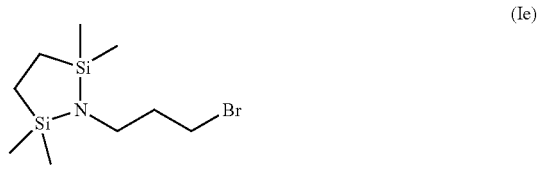

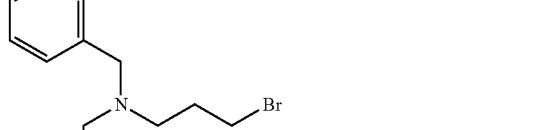

In the general formulas, "TMS" means trimethyl silyl, "TBS" means tert-butyl dimethylsilyl, and "Boc" means tert-butoxycarbonyl.

[Polymer Synthesis Example 1] Synthesis of Polymer (VIa)

A stirring bar was placed in a 2 L four neck flask connected to a thermometer, a dripping funnel, and a Dimroth condenser. After the degree of vacuum in the device was held at 10 Pa or less, the internal part of the device was heated with an oil bath and a heat gun, so that the water content in the system was removed. Subsequently, 4.96 g (1.05 mmol/g) of the THF solution of the polymerization initiator (Va) produced in the above-described [Synthesis Example 1] and 420 g of distilled THF were added into the 2 L four neck flask under a nitrogen stream.

Into the dripping funnel, 60 g of ethylene oxide and 120 g of distilled THF were injected, to be dripped into the 2 L four neck flask little by little. After confirming stabilization of the temperature in the 2 L four neck flask, the 2 L four neck flask was immersed in an oil bath held at a temperature of 45° C. for maturation for 8 hours. After completion of the reaction, the oil bath was detached and the reaction system was cooled to room temperature. A reaction scheme is shown in the following.

A small amount of the produced reaction system was sampled and quenched with acetic acid for measurement by GPC. The following results were obtained: Mw=8,500 and Mw/Mn=1.04.

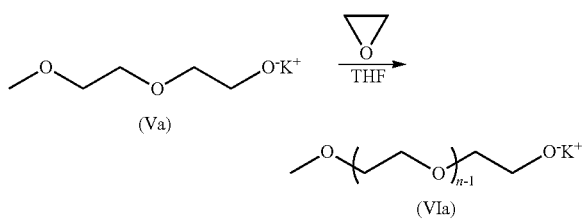

[Polymer Synthesis Example 1-1] Synthesis of Polymer (IXa)

A 2 L high pressure gas reaction vessel was dried by nitrogen purge, and 8.30 g (1.05 mmol/g, 8.72 mmol) of the THF solution of the polymerization initiator (Va) produced in the above-described [Synthesis Example 1] and 1008 g of distilled THP were added thereto under a nitrogen atmosphere. After the temperature in the reaction vessel was raised to 45° C., 112 g of ethylene oxide was continuously pressed into the reaction vessel, and the pressure in the system was then adjusted to 0.15 MPa by nitrogen pressurization. Stirring was performed at 45° C. to gradually lower the pressure of the system, and after 6 hours, the pressure of the system became stable at 0.11 MPa where the reaction was determined to be completed. Subsequently, the reaction was stopped with 0.32 g of H$_2$O, then adsorption treatment was performed by adding 10 g of KW-2000 (Kyowa Chemical Industry Co., Ltd.) and stirring the resulting mixture for 2 hours, and then KW-2000 was removed by filtration. The reaction solution was concentrated to 448 g, 1120 g of hexane was then placed in a 3 L beaker with a stirring bar therein, and after dripping the produced reaction liquid with a dripping funnel for 10 minutes, maturation was performed for 10 minutes. The produced white powder was filtered and then returned to the original beaker, to be washed with 560 g of hexane for 10 minutes, and the produced white powder was vacuum-dried to obtain 107 g of a polymer (IXa). The following GPC measurement results were obtained: Mw=12500 and Mw/Mn=1.02. A reaction scheme is shown in the following.

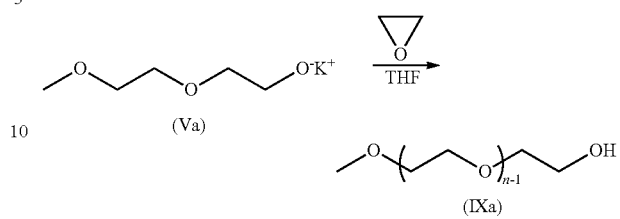

[Polymer Synthesis Example 2] Synthesis of Polymer (IIa)

Into a 100 ml dried three neck flask, 26 g (2.6 g in terms of solid content) of the THF solution of the polymer (VIa) produced in the [Polymer Synthesis Example 1] was fractionated with a syringe. Under a nitrogen stream, 0.298 g of the electrophile (Ia) and 0.43 ml of a THF solution (1 mol/L) of potassium tert-butoxide were added, and with the temperature in the flask being held at 40° C., maturation was performed for 5 hours. After completion of the reaction, filtration was performed while holding the temperature at 40° C., and a precipitated salt was removed. In a 200 mL beaker with a stirring bar therein, 26 g of hexane was placed, and after dripping the produced reaction liquid with a dripping funnel for 5 minutes, maturation was performed for 10 minutes. The produced white powder was filtered and then returned to the original beaker, to be washed with 13 g of hexane for 10 minutes. The same washing operation was further performed once.

The produced white powder was vacuum-dried to obtain 2.30 g of a polymer (IIa). The following GPC measurement results were obtained: Mw=8800 and Mw/Mn=1.04. A reaction scheme is shown in the following.

The reaction of the polymer (VIa) with an electrophile was subsequently performed without purifying the polymer (VIa), and therefore it is revealed that the present synthesis example has a substantially simplified process.

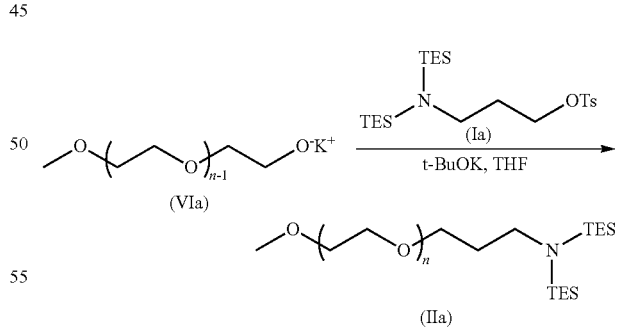

[Polymer Synthesis Example 2-1] Synthesis of Polymer (IIa)

A 2 L high pressure gas reaction vessel was dried by nitrogen purge, and 8.30 g (1.05 mmol/g, 8.72 mmol) of the THF solution of the polymerization initiator (Va) produced in the above-described [Synthesis Example 1] and 1008 g of distilled THP were added thereto under a nitrogen atmosphere. After the temperature in the reaction vessel was raised to 45° C., 112 g of ethylene oxide was continuously pressed into the reaction vessel, and the pressure in the system was then adjusted to 0.15 MPa by nitrogen pressurization. Stirring was performed at 45° C. to gradually lower the pressure of the system, and after 6 hours, the pressure of the system became stable at 0.11 MPa where the reaction was determined to be completed. After the reaction system was cooled to 40° C., 8.14 g of the electrophile (Ia) was dissolved in 81.4 g of THF, and the resultant mixture was pressed into the system, and, further, 8.9 ml of a THF solution (1 mol/L) of potassium tert-butoxide was diluted with 50 g of THF, and the resultant solution was pressed into the system. Subsequently, with the temperature being held at 40° C., maturation was performed for 5 hours. A precipitated salt was separated by filtration, and 11 g of an adsorption material KW-2000 was added to the filtrate, stirring was performed for 2 hours, and the adsorption material was then removed by filtration. The reaction solution was concentrated to 448 g. 1120 g of hexane was then placed in a 3 L beaker with a stirring bar therein, and after dripping the produced reaction solution with a dripping funnel for 10 minutes, maturation was performed for 10 minutes. The produced white powder was filtered and then returned to the original beaker, to be washed with 560 g of hexane for 10 minutes, and after the same washing was repeated once again, the produced white powder was vacuum-dried to obtain 109 g of a polymer (IIa). The following GPC measurement results were obtained: Mw=12900 and Mw/Mn=1.02. A reaction scheme is shown in the following.

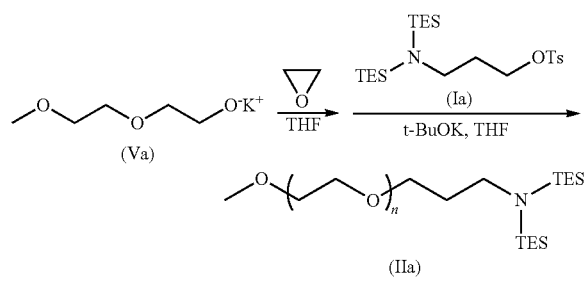

It is revealed that the polymerization with ethylene oxide stoichiometrically progresses in the Polymer Synthesis Example 1-1 and the Polymer Synthesis Example 2-1 as shown in Table 1 below.

TABLE 1

| | Theoretical Mw | Mw | Mw/Mn | Yield rate (%) |
|---|---|---|---|---|
| Polymer Synthesis Example 1-1 | 13,000 | 12,500 | 1.02 | 94.4 |
| Polymer Synthesis Example 2-1 | 13,300 | 12,900 | 1.02 | 94.1 |

[Polymer Synthesis Example 3] Synthesis of Polymer (IIa)

Into a 50 ml three neck flask, 10 g of the Polymer (IIa) produced in the [Polymer Synthesis Example 2], 9.0 g of THF and 0.4 ml of 1N HCl aq. were fed, and stirring was performed at 40° C. for 4 hours. The reaction was then stopped with 0.2 ml of 25 wt. % NaOH aq. After the reaction solution was concentrated to evaporate water, a polymer solution was prepared with 5.7 g of THF, and a precipitated salt was filtered. In a 100 mL beaker with a stirring bar therein, 10 g of hexane was placed, and after dripping the produced reaction solution, maturation was performed for 10 minutes. The produced white powder was filtered and then returned to the original beaker, to be washed with 5 g of hexane for 10 minutes. The same washing operation was further performed once.

The produced white powder was vacuum-dried to obtain 0.7 g of a polymer (IIIa). The following GPC measurement results were obtained: Mw=8500 and Mw/Mn=1.05. A reaction scheme is shown in the following.

Deprotection may subsequently be performed by adding hydrochloric acid without purifying the polymer (IIa) after the reaction in the [Polymer Synthesis Example 2], and in that case, the process was able to be further simplified.

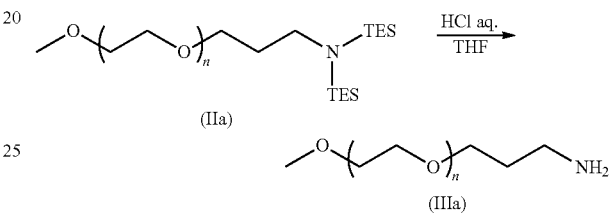

[Polymer Synthesis Example 3-1] Synthesis of Polymer (IIIa)

Into a 1 L three neck flask, 100 g of the polymer (IIa) produced in the [Polymer Synthesis Example 2-1], 400 g of MeOH, and 5.00 g of acetic acid were fed, and stirring was performed at 35° C. for 3 hours. The reaction was then stopped with 24.12 g of a 28% solution of sodium methylate in methanol. The reaction solution was concentrated, and solvent substitution with toluene was performed, so that 450 g of a polymer solution was prepared, and a precipitated salt was filtered. To the produced polymer solution, 100 g of the adsorption material KW-2000 was added, and treatment was performed at 35° C. for 1 hour to remove trace amount of the salt. In a 3 L beaker with a stirring bar therein, 1000 g of hexane and 500 g of ethyl acetate were placed, and after dripping the produced reaction solution, maturation was performed for 10 minutes. The produced white powder was filtered and then returned to the original beaker, to be washed with 600 g of hexane and 300 g of ethyl acetate for 10 minutes, and the same washing operation was further performed once.

The produced white powder was vacuum-dried to obtain 90 g of a polymer (IIIa). The following GPC measurement results were obtained: Mw=13,000 and Mw/Mn=1.02. A reaction scheme is shown in the following.

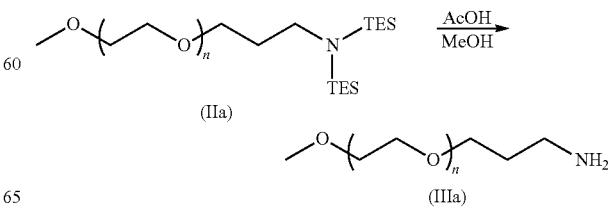

[Polymer Synthesis Example 4] Purification of Polymer (IIIa)

The inside of a cartridge filled with 50 g of a cation exchange resin DIAION PK-208 (made by Mitsubishi Chemical Corporation) was washed with 300 g of 1N hydrochloric acid, and then washed 3 times with 300 g of ion-exchanged water, and subsequently once with 300 g of methanol. Into a 500 mL two neck flask, a 5 wt. % solution of the polymer (IIIa) obtained in the [Polymer Synthesis Example 3] in methanol (polymer content; 10 g) was injected, and transferred into the cartridge with a pump. The methanol solution discharged from the liquid outlet of the cartridge was added into the original 500 mL round-bottom flask. The operation was continuously performed for 2 hours, so that the polymer (IIa) was adsorbed to the cation exchange resin. Subsequently the resin in the cartridge was washed with 300 g of methanol once, and then the polymer (IIIa-2) was eluted from the cation exchange resin with 50 g of 7N ammonia solution (methanol solution made by Kanto Chemical Co., Ltd.). The purified polymer after the process of elution from the cation exchange resin is denoted as ("IIIa-2").

Even when the polymer (IIa) is used directly in place of the polymer (IIa), deprotection progresses in the methanol solution in the presence of the cation exchange resin catalyst, and therefore both deprotection and purification may be performed in parallel, and the process was able to be further simplified.

The produced eluent was transferred into a 500 mL round-bottom flask, and ammonia and methanol were distilled away with a rotary evaporator. Through vacuum concentration almost to dryness, the solvent was substituted with toluene such that the solid content concentration of the polymer (IIIa-2) was adjusted to 25 wt. %.

In a 500 mL beaker with a stirring bar therein, 100 g of hexane and 50 g of ethyl acetate were mixed. After dripping of a 25 wt. % produced polymer (IIIa-2) solution for 10 minutes with a dripping funnel, stirring was performed for 20 minutes, and maturation was performed. The produced white powder was filtered and then returned to the original beaker, to be washed with a mixed solvent of 50 g of hexane and 25 g of ethyl acetate for 20 minutes. The same washing operation was further performed once.

The produced white powder was vacuum-dried to obtain 8.51 g of a polymer (IIIa-2). The following GPC measurement results were obtained: Mw=8,500 and Mw/Mn=1.05.

[Polymer Synthesis Example 5] Synthesis of Polymers (VIb) to (VIf)

Polymers (VIb) to (VIf) were synthesized by approximately the same operations as in the [Polymer Synthesis Example 1], except that the amount of the polymerization initiator (Va) used (1.05 mmol/g THF solution) was changed. The analysis results are shown in Table 2.

TABLE 2

|  | Polymerization initiator (Va) amount (g) | Mw | Mw/Mn |
| --- | --- | --- | --- |
| Polymer (VIa) | 4.96 | 8,500 | 1.04 |
| Polymer (VIb) | 4.50 | 9,400 | 1.05 |
| Polymer (VIc) | 4.00 | 10,500 | 1.06 |
| Polymer (VId) | 3.50 | 12,000 | 1.05 |
| Polymer (VIe) | 3.00 | 14,000 | 1.06 |
| Polymer (VIf) | 2.50 | 16,900 | 1.05 |

[Polymer Synthesis Example 6] Synthesis of Polymers (IIb) to (IIf)

Polymers (IIb) to (IIf) were synthesized by approximately the same operations as in the [Polymer Synthesis Example 2], except that the polymer (VIa) as a starting raw material was changed to the polymers (VIb) to (VIf). The analysis results are shown in Table 3.

TABLE 3

|  | Mw | Mw/Mn | Starting raw material polymer |
| --- | --- | --- | --- |
| Polymer (IIa) | 8,800 | 1.04 | Polymer (VIa) |
| Polymer (IIb) | 9,600 | 1.05 | Polymer (VIb) |
| Polymer (IIc) | 10,800 | 1.06 | Polymer (VIc) |
| Polymer (IId) | 12,300 | 1.05 | Polymer (VId) |
| Polymer (IIe) | 14,200 | 1.06 | Polymer (VIe) |
| Polymer (IIf) | 17,100 | 1.05 | Polymer (VIf) |

[Polymer Synthesis Example 7] Synthesis of Polymers (IIIb) to (IIIf)

Polymers (IIIb) to (IIIf) were synthesized by approximately the same operations as in the [Polymer Synthesis Example 3] and the [Polymer Synthesis Example 4], except that the polymer (IIa) as a starting raw material was changed to the polymers (IIb) to (IIf). The analysis results are shown in Table 4.

TABLE 4

|  | Mw | Mw/Mn | Starting raw material polymer |
| --- | --- | --- | --- |
| Polymer (IIIa) | 8,500 | 1.05 | Polymer (IIa) |
| Polymer (IIIb) | 9,400 | 1.05 | Polymer (IIb) |
| Polymer (IIIc) | 10,500 | 1.06 | Polymer (IIc) |
| Polymer (IIId) | 12,100 | 1.05 | Polymer (IId) |
| Polymer (IIIe) | 14,000 | 1.06 | Polymer (IIe) |
| Polymer (IIIf) | 16,800 | 1.05 | Polymer (IIF) |

[Polymer Synthesis Example 8] Synthesis of Polymers (IIIg) to (IIIn)

Polymers (IIIg) to (IIIn) were synthesized by approximately the same operations as in the [Polymer Synthesis Example 1] to the [Polymer Synthesis Example 4], except that the deprotection condition was changed by changing the electrophile from (Ia) to (Ib) to (Ii) in the [Polymer Synthesis Example 2]. The deprotection in the case in which the electrophiles (Ib) to (Ie), and (Ii) were used was performed in the same manner as in the Polymer Synthesis Example 3. The deprotection in the case in which electrophiles (If) and (Ih) were used was performed under the condition of Birch reduction in which liquid ammonium and metal sodium were used. The deprotection in the case in which the electrophile (Ig) was used was performed by reacting a hydrazine hydrate in an alcohol. The analysis results are shown in Table 5.

TABLE 5

|  | Mw | Mw/Mn | Electrophile used |
|---|---|---|---|
| Polymer (IIIg) | 8,500 | 1.05 | Ib |
| Polymer (IIIh) | 8,500 | 1.05 | Ic |
| Polymer (IIIi) | 8,500 | 1.05 | Id |
| Polymer (IIIj) | 8,600 | 1.06 | Ie |
| Polymer (IIIk) | 8,600 | 1.05 | If |
| Polymer (IIIl) | 8,500 | 1.06 | Ig |
| Polymer (IIIm) | 8,700 | 1.05 | Ih |
| Polymer (IIIn) | 8,700 | 1.05 | Ii |

[Comparative Polymer Synthesis Example 1]
Synthesis of Polymer (IXa)

A stirring bar and 71 mg (1.01 mmol) of potassium methoxide (made by Kanto Chemical Co., Ltd.) as a polymerization initiator was placed in a 500 mL four neck round-bottom flask connected to a thermometer, a dripping funnel, and a Dimroth condenser. After the degree of vacuum in the device was held at 10 Pa or less, the internal part of the device was heated with an oil bath and a heat gun, so that the water content in the system was removed.

Subsequently 40 µL (1.00 mmol) of methanol (made by Tokyo Chemical Industry Co., Ltd.) and 140 g of distilled THF were injected in the four neck flask under nitrogen stream, and the mixture was stirred at room temperature until potassium methoxide was completely dissolved. The ratio of the amounts of substances between potassium methoxide being the polymerization initiator synthesized by the above-described method and methanol being the alcohol as an initiator raw material is 50:50 (mol %).

Into the dripping funnel, a mixed solution of 35 g of ethylene oxide and 60 g of distilled THF were injected, to be dripped into the four neck flask slowly, with the inner temperature being held at 35° C. or lower. After dripping of the entire quantity, the mixture was stirred for 80 hours, with the inner temperature being held at 50° C. or lower.

After confirming no change in conversion ratio of ethylene oxide, 0.06 g of acetic acid was added into the flask. After removal of ethylene oxide by nitrogen bubbling, the reaction liquid was transferred into a 500 mL round-bottom flask, and concentrated until solid precipitated with a rotary evaporator. The crude product of polymer in an amount of 23 g was redissolved in 46 g of toluene, and transferred into a dripping funnel.

Into a 500 mL beaker with a stirring bar therein, 138 g of isopropyl ether was injected. After dripping of the polymer solution for 10 minutes with a dripping funnel, maturation was performed for 20 minutes. The produced white powder was filtered and returned to the original beaker, to be washed with a mixed solvent of 69 g of isopropyl ether for 20 minutes. The same washing operation was further performed twice. A reaction scheme is shown in the following.

The produced white powder was vacuum-dried to obtain 18.54 g of a comparative polymer (IXa). The following GPC measurement results were obtained: Mw=7,200 and Mw/Mn=1.16.

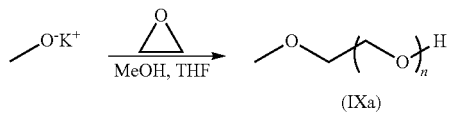

(IXa)

[Comparative Polymer Synthesis Example 2]
Synthesis of Polymer (Xa)

A stirring bar was placed in a 500 mL four neck flask connected to a thermometer, a Dimroth condenser, a fractionating column, and a 300 mL round-bottom flask. After the degree of vacuum in the device was held at 10 Pa or less, the internal part of the device was heated with an oil bath and a heat gun, so that the water content in the system was removed. The THF solution of the polymer (VIa) (10 g in terms of solid content) was fractionated with a syringe and fed into the 500 mL four neck flask under nitrogen stream. With the temperature in the 500 mL four neck flask being held at 40° C. or lower, the polymer solution was concentrated and adjusted to be a solid content concentration of 25 wt. %.

Under a nitrogen stream, 1.0 g of acrylonitrile was fed in the 500 mL four neck flask, so that maturation was performed for 3 hours, with the temperature in the 500 mL four neck flask being held at 40° C. After completion of the reaction, the oil bath was detached and the reaction system was cooled to room temperature. After addition of 0.2 g of acetic acid into the system for quenching, 10 g of an alkali adsorbent "KYOWADO 700" (made by Kyowa Chemical Industry Co., Ltd.) was added for performing a reaction for 3 hours. After filtration of the alkali adsorbent, the filtrate was transferred into a 300 mL round-bottom flask and concentrated to a solid content concentration of a comparative polymer (Xa) of 25 wt. % with a rotary evaporator.

In a 500 mL beaker with a stirring bar therein, 100 g of hexane and 50 g of ethyl acetate were mixed. After dripping of the concentrated liquid for 10 minutes with a dripping funnel, maturation was performed for 20 minutes. The produced white powder was filtered and then returned to the original beaker, to be washed with a mixed solvent of 50 g of hexane and 25 g of ethyl acetate for 20 minutes. The same washing operation was further performed once. A reaction scheme is shown in the following.

The produced white powder was vacuum-dried to obtain 9.12 g of a comparative polymer (Xa). The following GPC measurement results were obtained: Mw=8,800 and Mw/Mn=1.05.

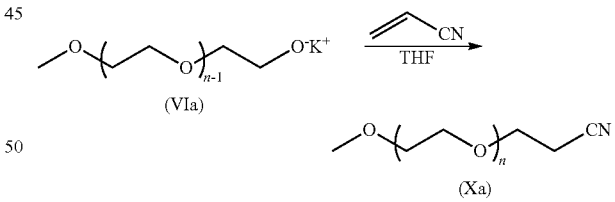

[Comparative Polymer Synthesis Example 3]
Synthesis of Polymer (IIIo)

Into a 500 mL autoclave for hydrogen reduction, 5.0 g of a polymer (Xa), 5.0 g of Raney cobalt catalyst R-400 (made by Nikko Rica Corporation), 45.0 g of methanol, and 3.5 mL of 1 N methanol solution of ammonia (made by Aldrich) were injected at room temperature. Subsequently hydrogen gas (pressure: 10 kg/cm$^2$) was enclosed, and the inner temperature was raised to 120° C. for a direct reaction for 6 hours. After cooling to room temperature, the pressure was returned to atmospheric pressure. Subsequently nitrogen was blown in for removal of ammonia in the system. After removal of the Raney cobalt catalyst by filtration, the filtrate was transferred into a 100 mL round-bottom flask, and ammonia and methanol were distilled away with a rotary evaporator. Through vacuum concentration to dryness, 4.5 g of a mixture of a polymer (IIIo) and the compounds represented by the following formula (VIIo) to (IXo) were obtained. The following GPC measurement results were obtained: Mw=8,900 and Mw/Mn=1.11. A reaction scheme and by-products are shown in the following.

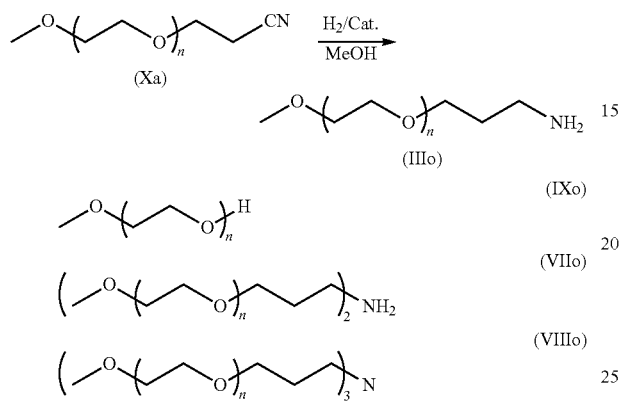

Analysis of Content of Impurities in Products Produced in Polymer Synthesis Example 3 and Comparative Polymer Synthesis Example 3

The content of impurities in the product produced in the [Polymer Synthesis Example 3] and in the product produced in the [Comparative Polymer Synthesis Example 3] were analyzed. The results are shown in Table 6 below.

A compound represented by "mPEG" in Table 6 is a compound corresponding to the general formula (IXo) in the [Comparative Polymer Synthesis Example 3] and is a compound produced through β-elimination of acrylonitrile from a polymer having a cyanoethyl group at an end. The compositional ratio of mPEG was calculated by H-NMR measurement. First of all, each of the products produced in the [Polymer Synthesis Example 3] and in the [Comparative Polymer Synthesis Example 3] was weighed by 10 mg, and each of these is dissolved in 0.75 ml of CDCl3, then 50 mg of trifluoroacetic anhydride was added thereto, and after the resultant mixture was left standing for 1 day, the measurement was conducted. The compositional ratio of mPEG was calculated from the ratio between a proton originated from α-methylene of an ester in the compound represented by the general formula (IX-1) produced through the treatment and a proton originated from α-methylene of an amide in the compound represented by the general formula (III-1) also produced from the treatment.

Compounds represented by "secondary and tertiary amines" in Table 6 are compounds corresponding to the general formulas (VIIo) and (VIIIo) in the [Comparative Polymer Synthesis Example 3] respectively. The amount of the compounds mixed was measured by GPC and was calculated from the area percentages of the polymers having twice or three times as large as the molecular weight.

From these results, β-elimination of acrylonitrile and production of secondary and tertiary amines due to hydrogen reduction were observed in the comparative polymer (IIIo); however, these by-products were not observed in the example polymer (IIIa).

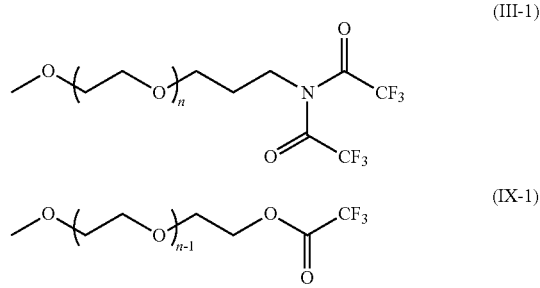

TABLE 6

|  | mPEG | Secondary and tertiary amines |
|---|---|---|
| Polymer (IIIa) | <1% | <1% |
| Comparative polymer (IIIo) | 10% | 5% |

Metal Analysis of Products Produced in Polymer Synthesis Examples 3 and 4, and Comparative Polymer Synthesis Example 3

Metal impurities in the products produced in each of the [Polymer Synthesis Example 3] and the [Polymer Synthesis Example 4], and in the product produced in the [Comparative Synthesis Example 3] were analyzed with a high frequency inductively coupled plasma mass spectrometer (ICP-MS, Agilent Technologies 7500 cs). The analysis was performed by a standard loaded method using samples each obtained by diluting a polymer with ultrapure water by 100 times for measurement. The analysis results (value obtained in terms of solid content) are shown in Table 7 (in units of ppb).

As a result of the metal analysis, it is revealed that the heavy metal used for reduction is mixed in the comparative polymer (IIIo), but that a heavy metal is not contained in the polymers (IIIa) and (IIIa-2) of the Examples because a heavy metal catalyst is not used in the synthesis process.

TABLE 7

|  | Co | Ni | Pd | Pt | Rh | Ru | Cu | Cr | K |
|---|---|---|---|---|---|---|---|---|---|
| Polymer (IIIa) | <1 | <1 | <1 | <1 | <1 | <1 | <1 | <1 | 7000 |
| Polymer (IIIa-2) | <1 | <1 | <1 | <1 | <1 | <1 | <1 | <1 | 100 |
| Comparative polymer (IIIo) | 200 | <1 | <1 | <1 | <1 | <1 | <1 | <1 | 8000 |

[Synthesis Example 5] Synthesis of Polymerization Initiators (Vb) to (Vg)

Polymerization initiators (Vb) to (Vg) were synthesized in the same method as described in [Synthesis Example 1], except that the raw material alcohol was changed to alcohols in the table below.

TABLE 8

| | Raw material alcohol |
|---|---|
| Polymerization initiator (Vb) | Triethylene glycol monomethyl ether |
| Polymerization initiator (Vc) | Diethylene glycol monoethyl ether |
| Polymerization initiator (Vd) | Triethylene glycol monoethyl ether |
| Polymerization initiator (Ve) | Diethylene glycol monopropyl ether |
| Polymerization initiator (Vf) | Diethylene glycol mono-tert-butyl ether |
| Polymerization initiator (Vg) | Triethylene glycol monocyclohexyl ether |

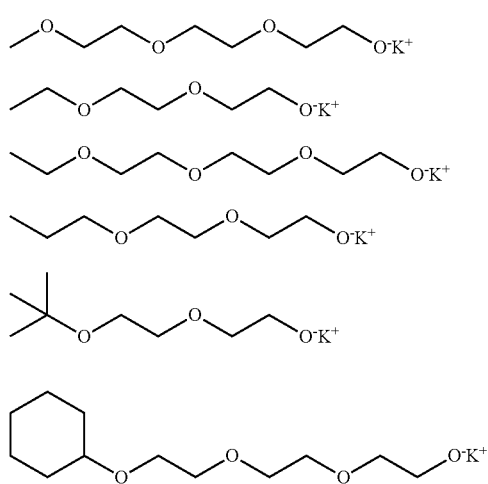

[Comparative Synthesis Example 1] Synthesis of Comparative Polymerization Initiators (Vh) to (Vk)

Comparative polymerization initiators (Vh) to (Vk) were synthesized in the same method as described in [Synthesis Example 1], except that the raw material alcohol was changed to alcohols in the table below.

TABLE 9

| | Raw material alcohol |
|---|---|
| Comparative polymerization initiator (Vh) | Methanol |
| Comparative polymerization initiator (Vi) | Ethanol |
| Comparative polymerization initiator (Vj) | 1-Propanol |
| Comparative polymerization initiator (Vk) | Cyclohexanol |

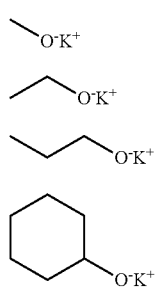

Comparison of Solubility of Polymerization Initiators Produced in Synthesis Examples 1 and 5, and Comparative Synthesis Example 1 to Polymerization Solvent Subsequently, the results of the solubility of the polymerization initiators (Va) to (Vg) and the comparative polymerization initiators (Vh) to (Vk) to the polymerization solvent are shown. The results of dissolving each polymerization initiator at a concentration of 20 wt. % in THF as a polymerization solvent are shown in the Table 10. An initiator for which cloudiness was not observed at all by visual observation, when dissolved, was denoted as "Excellent", and an initiator for which cloudiness was observed, when dissolved, or the initiator that did not dissolve at all was denoted as "Poor". As a result thereof, the initiators (Va) to (Vg), each having a long chain, dissolved in the solvent. On the other hand, the comparative initiators (Vh) to (Vk) did not dissolve in the solvent.

TABLE 10

| | | THF |
|---|---|---|
| Initiator | Va | Excellent |
| | Vb | Excellent |
| | Vc | Excellent |
| | Vd | Excellent |
| | Ve | Excellent |
| | Vf | Excellent |
| | Vg | Excellent |
| Comparative initiator | Vh | Poor |
| | Vi | Poor |
| | Vj | Poor |
| | Vk | Poor |

It is revealed that, in the [Polymer Synthesis Example 1] and in the [Comparative Polymer Synthesis Example 1], the latter requires a long polymerization time, as long as 80 hours, due to the presence of an alcohol as an initiator raw material, and that, in the former, the polymerization reaction is completed within 8 hours by using an initiator that is soluble in THF even when the amount of residual alcohol as an initiator raw material is small. That is to say, the polymerization of an alkylene oxide under mild conditions was realized by the method of the present invention. Moreover, by using the reaction liquid in the [Polymer Synthesis Example 1] directly to the reaction in the [Polymer Synthesis Example 2], the process was able to be substantially simplified. Furthermore, by using an organic solvent for purifying a resin with an ion exchange resin in [Polymer Synthesis Example 4], it became possible to purify a polymer by a simple method without using freeze dry in the final process.

Hydrogenation reaction using a heavy metal as a catalyst is required for reducing a cyano group in the [Comparative Polymer Synthesis Examples 2 and 3]; however, in the [Polymer Synthesis Examples 2 and 3], the electrophiles the amino group of which is protected by a protecting group are used, and therefore the intended polymers were able to be synthesized only by performing deprotection. In the comparative polymer (IIIo), β-Elimination of acrylonitrile and production of secondary and tertiary amines due to hydrogen reduction occurred; however, in the example polymer (IIa), production of any one of the amines were not observed (Table 6).

Moreover, from the results of metal analysis, it is revealed that, in the [Polymer Synthesis Examples 3 and 4] and in the [Comparative Polymer Synthesis Example 3], the heavy metal used for reduction is mixed in the comparative polymer (IIIo), but that a heavy metal is not substantially mixed in the example polymers (IIIa and IIIa-2) because no heavy metal is used in [Synthesis Examples 3 and 4] (Table 7). Moreover, the amount of a K metal mixed was able to be reduced by the purification with a strong acid cation exchange resin. As a result thereof, synthesis of an amino group-containing narrowly distributed polyalkylene glycol derivative without mixing of a heavy metal having a possibility that causes adverse influence in medical supplies was able to be achieved by the present invention. Moreover, in the present invention, polymerization of an alkylene oxide, terminal-stopping reaction with an electrophile, and subsequent deprotection may be performed continuously, so that the simplification of the process was also achieved.

The method for producing an amino group-containing narrowly distributed and high-purity polyalkylene glycol derivative of the present invention provides a raw material of block copolymers for use in medical supplies and cosmetic products.

Having thus described certain embodiments of the present invention, it is to be understood that the invention defined by the appended claims is not to be limited by particular details set forth in the above description as many apparent variations thereof are possible without departing from the spirit or scope thereof as hereinafter claimed.

What is claimed is:

1. A method for producing a polyalkylene glycol derivative having an amino group at an end, comprising the following [Step 1] to [Step 4]:

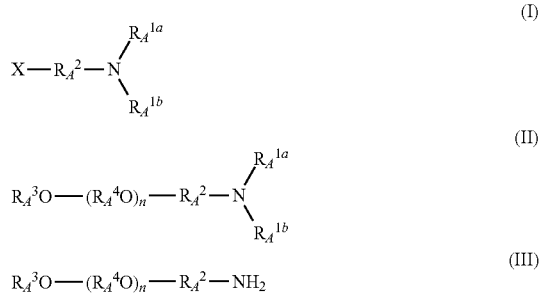

wherein $R_A^{1a}$ and $R_A^{1b}$ each independently represent a protective group of the amino group, or one of $R_A^{1a}$ and $R_A^{1b}$ represents a hydrogen atom and the other represents a protective group of the amino group, or $R_A^{1a}$ and $R_A^{1b}$ bind to each other to represent a cyclic protective group forming a ring together with a nitrogen atom of the amino group, and the protective group represents a protective group deprotectable without using a heavy metal catalyst;

$R_A^2$ represents a linear divalent hydrocarbon group having 1 to 6 carbon atoms, or a branched or cyclic divalent hydrocarbon group having 3 to 6 carbon atoms;

$R_A^3$ represents a linear hydrocarbon group having 1 to 20 carbon atoms, or a branched or cyclic hydrocarbon group having 3 to 20 carbon atoms;

$R_A^4$ represents an alkylene group having 2 to 8 carbon atoms;

X represents a leaving group; and n represents an integer of 3 to 450;

[Step 1]

a step of reacting a compound of formula (IV) with an alkali metal or an alkali metal compound selected from M, $M^+H^-$, $R_X^-M^+$, $[R_Y]^-M^+$, and $R_Z O^-M^+$ (wherein M represents an alkali metal, $R_X$ represents an alkyl group having 1 to 20 carbon atoms or an arylalkyl group having 7 to 20 carbon atoms, $R_Y$ represents an aromatic compound that may have a substituent, and $R_Z$ represents an alkyl group having 1 to 6 carbon atoms) to obtain a compound of formula (V):

wherein $R_A^3$ and $R_A^4$ are the same as defined formulas (II) and (III);

k represents an integer of 2 to 5;

wherein $R_A^3$, $R_A^4$, and k are the same as defined in formula (IV); and

M is the same as defined for the alkali metal or the alkali metal compound;

[Step 2]

a step of reacting the compound of formula (V) with an alkylene oxide in a polymerization solvent to obtain a compound of formula (VI):

wherein $R_A^3$, $R_A^4$, and n are the same as defined in formulas (II) and (III); and M is the same as defined for the alkali metal or the alkali metal compound;

[Step 3]

a step of reacting the compound of formula (VI) with the electrophile of formula (I) to obtain the compound of formula (II), wherein the electrophile of formula (I) used in the [Step 3] is an electrophile of formula (I-I-I):

wherein $R^1$ each independently represent a linear monovalent hydrocarbon group having 1 to 6 carbon atoms, or a branched or cyclic monovalent hydrocarbon group having 3 to 6 carbon atoms, or $R^1$ may bind to each other to form a 3 to 6 membered ring together with a silicon atom having bonds with $R^1$; and $R_A^2$ and X are the same as defined in formula (I); and

[Step 4]

a step of deprotecting the compound of formula (II) without using a heavy metal catalyst to obtain the compound of formula (III).

2. The method according to claim 1, wherein, in the [Step 3], the compound obtained in the [Step 2] of formula (VI) is reacted with the electrophile of formula (I) without performing purification of the compound of formula (VI).

3. The method according to claim 1, wherein, in the [Step 1], the compound of formula (IV) is reacted with the alkali metal or the alkali metal compound so that a ratio of the amounts of substances between the compound of formula (V) and the compound of formula (IV) is 100:0 to 80:20 after the compound of formula (V) is synthesized from the compound of formula (IV).

4. The method according to claim 1, wherein, in the [Step 1], a ratio of the amounts of substances between the compound of formula (V) and the compound of formula (IV) is set to 100:0 to 98:2 by distilling away the compound of formula (IV) under reduced pressure after the compound of formula (V) is synthesized from the compound of formula (IV).

5. The method according to claim 1, wherein the [Step 2] further comprises dissolving a reaction product obtained in the [Step 1] in the polymerization solvent.

6. The method according to claim 1, wherein the [Step 2] is performed at a reaction temperature in the range of 30 to 60° C.

7. The method according to claim 1, wherein, in the [Step 3], an amount of the electrophile of formula (I) used is 1 to 20 equivalents relative to a number of moles of the compound of formula (VI).

8. The method according to claim 1, wherein the [Step 3] further comprises:
stopping reaction of the compound obtained in the [Step 2] of formula (VI) by an acid compound or a protic compound to obtain a compound of formula (IX); and
purifying the obtained compound of formula (IX), and
the reaction of the compound of formula (VI) with the electrophile of formula (I) in the [Step 3] is performed by an operation of reacting the purified compound of formula (IX) with the electrophile of formula (I) in the presence of a basic compound:

wherein $R_A^3$, $R_A^4$, and n are as the same as defined in formulas (II) and (III).

9. The method according to claim 1, wherein a content of a heavy metal impurity in the reaction product comprising the compound of formula (III) obtained in the [Step 4] is 100 ppb or less, and the heavy metal impurity comprises one or more selected from the group consisting of Co, Ni, Pd, Pt, Rh, Ru, Cu, and Cr.

10. The method according to claim 1, wherein the [Step 4] further comprises:
reacting a reaction product comprising the compound of formula (III) with a basic compound to produce a salt after the compound of formula (III) is obtained, and thereafter removing the produced salt by filtration.

11. The method according to claim 1, wherein the [Step 4] further comprises:
reacting a reaction product comprising the compound of formula (III) with a basic compound to produce a salt after the compound of formula (III) is obtained, and thereafter removing the produced salt using an adsorption material.

12. The method according to claim 1, further comprising the following [Step 5] to [Step 8] after the [Step 3] or the [Step 4]:
[Step 5]
a step of reacting a product in the [Step 3] or the [Step 4] with a strong acid cation exchange resin and then washing the strong acid cation exchange resin to separate a substance other than the compound of formula (III);
[Step 6]
a step of reacting the strong acid cation exchange resin with a basic compound to separate the compound of formula (III);
[Step 7]
a step of concentrating a reaction liquid obtained in the [Step 6]; and

[Step 8]
a step of dripping a concentrated liquid obtained in the [Step 7] into a poor solvent for the compound of formula (III) to precipitate, thereby obtaining the compound of formula (III).

13. The method according to claim 1, wherein the [Step 2] further comprises:
confirming that the compound of formula (V) has been dissolved in the polymerization solvent before the reaction with the alkylene oxide, by checking that no cloudiness in the polymerization solvent is observed by visual observation.

14. The method according to claim 13, wherein a mass of the polymerization solvent is equal to or less than 10 times the mass of the compound of formula (V), in confirming that the compound of formula (V) has been dissolved in the polymerization solvent.

15. The method according to claim 1, wherein an area content ratio between a compound of formula (VII) and a compound of formula (VIII) in a reaction product comprising the compound of formula (III) obtained in the [Step 4] is 3% or less as measured by gel permeation chromatography, and a content ratio in terms of composition ratio of a compound of formula (IX) in the reaction product is 2 mol % or less as measured by proton nuclear magnetic resonance:

wherein $R_A^2$, $R_A^3$, $R_A^4$, and n are the same as defined for formulas (I) to (III).

16. A method for producing a polyalkylene glycol derivative of formula (II), comprising the following [Step 1] to [Step 3]:
[Step 1]
a step of reacting a compound of formula (IV) with an alkali metal or an alkali metal compound selected from M, $M^+H^-$, $R_X^-M^+$, $[R_Y]^{\cdot-}M^+$, and $R_Z O^- M^+$ (wherein M represents an alkali metal, $R_X$ represents an alkyl group having 1 to 20 carbon atoms, or an arylalkyl group having 7 to 20 carbon atoms, $R_Y$ represents an aromatic compound that may have a substituent, and $R_Z$ represents an alkyl group having 1 to 6 carbon atoms) to obtain a compound of formula (V):

wherein $R_A^3$ represents a linear hydrocarbon group having 1 to 20 carbon atoms, or a branched or cyclic hydrocarbon group having 3 to 20 carbon atoms; and
$R_A^4$ represents an alkylene group having 2 to 8 carbon atoms, and
k represents an integer of 2 to 5;

wherein $R_A^3$, $R_A^4$, and k are the same as defined in formula (IV); and
M is the same as defined for the alkali metal or the alkali metal compound;

[Step 2]
a step of reacting the compound of formula (V) with an alkylene oxide in a polymerization solvent to obtain a compound of formula (VI):

where $R_A^3$ and $R_A^4$ are the same as defined in formula (IV);

M is the same as defined for the alkali metal or the alkali metal compound; and n represents an integer of 3 to 450; and

[Step 3]

a step of reacting the compound of formula (VI) with an electrophile of formula (I-I-I) to obtain a compound of formula (II):

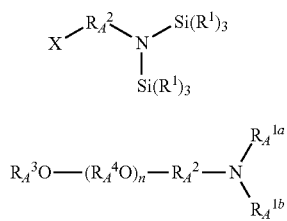

(I-I-I)

(II)

wherein $R^1$ each independently represent a linear monovalent hydrocarbon group having 1 to 6 carbon atoms, or a branched or cyclic monovalent hydrocarbon group having 3 to 6 carbon atoms, or $R^1$ may bind to each other to form a 3 to 6 membered ring together with a silicon atom having bonds with $R^1$;

$R_A^2$ represents a linear divalent hydrocarbon group having 1 to 6 carbon atoms, or a branched or cyclic divalent hydrocarbon group having 3 to 6 carbon atoms;

X represents a leaving group;

$R_A^{1a}$ and $R_A^{1b}$ each independently represent $-Si(R^1)_3$, wherein $R^1$ is as defined above;

$R_A^3$ and $R_A^4$ are the same as defined in formula (IV); and n represents an integer of 3 to 450.

* * * * *

UNITED STATES PATENT AND TRADEMARK OFFICE
CERTIFICATE OF CORRECTION

PATENT NO. : 10,377,775 B2
APPLICATION NO. : 14/959088
DATED : August 13, 2019
INVENTOR(S) : Suka et al.

Page 1 of 1

It is certified that error appears in the above-identified patent and that said Letters Patent is hereby corrected as shown below:

In the Specification

Column 7, Line 26: Please correct "ap-tolyl" to read -- a p-tolyl --

Column 39, Line 15: Please correct "(IIa)" to read -- (IIIa) --

Column 39, Line 24: Please correct "(IIa)" to read -- (IIIa) --

Column 40, Table 4, Line 45: Please correct "(IIF)" to read -- (IIf) --

Column 46, Line 62: Please correct "(IIa)" to read -- (IIIa) --

Signed and Sealed this
Twenty-sixth Day of November, 2019

Andrei Iancu
*Director of the United States Patent and Trademark Office*